United States Patent
Nellemann et al.

[11] Patent Number: 5,900,636
[45] Date of Patent: May 4, 1999

[54] DUAL-MODE GAMMA CAMERA SYSTEM UTILIZING SINGLE-PHOTON TRANSMISSION SCANNING FOR ATTENUATION CORRECTION OF PET DATA

[75] Inventors: Peter Nellemann; Hugo Bertelsen, both of Pleasanton; Lingxiong Shao; Horace H. Hines, both of San Jose, all of Calif.

[73] Assignee: ADAC Laboratories, Milpitas, Calif.

[21] Appl. No.: 08/865,916

[22] Filed: May 30, 1997

[51] Int. Cl.$^6$ ............................... G01T 1/29; G21K 5/10
[52] U.S. Cl. .............................. 250/363.04; 250/363.03; 378/20
[58] Field of Search ................. 250/363.04, 363.03; 378/20, 9

[56] References Cited

U.S. PATENT DOCUMENTS

| | | |
|---|---|---|
| 5,296,708 | 3/1994 | Moyers et al. . |
| 5,444,252 | 8/1995 | Hug et al. . |
| 5,449,913 | 9/1995 | Chang ................................. 250/363.04 |
| 5,461,232 | 10/1995 | McCandless et al. . |
| 5,471,061 | 11/1995 | Moyers et al. . |
| 5,552,606 | 9/1996 | Jones et al. . |
| 5,565,684 | 10/1996 | Gullberg et al. . |
| 5,585,637 | 12/1996 | Bertelsen et al. . |
| 5,596,197 | 1/1997 | Jones et al. ......................... 250/363.04 |
| 5,600,145 | 2/1997 | Plummer ............................. 250/363.04 |
| 5,608,221 | 3/1997 | Bertelsen et al. . |

FOREIGN PATENT DOCUMENTS

| | | |
|---|---|---|
| 0 008 264 (A1) | 2/1980 | European Pat. Off. . |
| 54-24588 | 2/1979 | Japan . |

OTHER PUBLICATIONS

Siu K. Yu and Claude Nahmias, Single Photon Transmission Measurements in Positron Tomography using $^{137}$Cs, 1995, Hamilton (ON), 29 pages.

Karp, et al., Singles Transmission in Positron Emission Tomography using $^{137}$Cs, from 1995 IEEE Nuclear Science Symposium and medical Imaging Conference record vol. 13, University of Pennsylvania and UGM Medical Systems (Philadelphia, PA), pp. 1363–1367.

P. Nellemann et al., Performance Characteristics of a Dual Head Spect Scanner with Pet Capability, From 1995 IEEE Nuclear Science Symposium conference record vol. 3, ADAC Laboratories and UGM Laboratory, pp. 1751–1755.

Karp, et al., Singles Transmission in Volume–Imaging PET with a $^{137}$Cs Source, *Phys. Med. Biol.*, vol. 40, 1995, University of Pennsylvania and UGM Medical Systems (Philadelphia, PA), pp. 929–944.

(List continued on next page.)

*Primary Examiner*—Constantine Hannaher
*Attorney, Agent, or Firm*—Blakely, Sokoloff, Taylor & Zafman LLP

[57] ABSTRACT

A nuclear camera system includes a pair of detectors orientated 180 degrees apart about an axis of rotation for detecting radiation emitted from an object, a pair of single-photon radiation point sources for transmitting radiation through the object, each to a different detector, and a gantry supporting the detectors and the radiation sources. The gantry provides rotation of the detectors and the radiation source about the axis of rotation, such that the angular positions of the radiation source about the axis of rotation remain fixed relative to the angular positions of the detectors. The camera system further includes a processing system coupled to control the dectors and the radiation sources and to selectably configure the detectors for either coincidence or single-photon emission imaging. The processing system controls the detectors to acquire coincidence emission data of the object and controls the single-photon point sources to acquire transmission data of the object, wherein the radiation from the point sources has a fanbeam illumination profile. The processing system corrects the acquired coincidence emission data for attenuation using the transmission data.

31 Claims, 22 Drawing Sheets

OTHER PUBLICATIONS

R.A. De Kemp, et al., Design and Performance of 3D Photon Transmission Measurement on a Positron Tomograph with Continuously Rotating Detectors, International Meeting on Fully–Dimensional Image Reconstruction in Radiology and Nuclear Medicine, 1995, Ottowa and Hamilton (ON), Knoxville (TN, pp. 51–54.

Robert Anthony Dekemp, B.A.Sc., Attenuation Correction in Positron Emission Tomography Single Photon Transmission Measurement, Sep. 1992, Hamilton (ON), 106 Pgs.

Bailey, et al, Ecart–Art–13 A Continuously Rotating Pet Camera: Performance Characteristics, Initial Clinical Studies, and Installation Considerations in in a Nuclear Medicine Department, *European Journal of Nuclear Medicine,* vol. 24, No. 1, Jan. 1997, pp. 6–15.

Robert A. De Kemp, et al. Attenuation Correction in Pet Using Single Photon Transmission Measurement, *Med. Phys.,* vol. 21, No. 6, Jun. 1994, pp. 771–778.

G. Muehllehner, et al., "Performance Parameters of a Positron Imaging Camera," IEEE Transactions on Nuclear Science, vol.NS–23, No. 1, Feb. 1976, pp. 528–537.

Gerd Muehllehner, Positron Camera with Extended Counting Rate Capability, *Journal of Nuclear Medicine,* vol. 15, No. 7, Jul. 1975, pp. 653–657.

Karp, et al., Continuous–Slice Penn–Pet: A Positron Tomograph with Volume Imaging Capability, *Journal of Nuclear Medicine,* vol. 31, No. 5, May 1990, pp. 617–627.

R.J. Smith et al., "Singles Transmission Scans Performed Post–Injection for Quantitative Whole Body PET Imaging," IEEE Nuclear Science Symposium Conference Record, vol. 3, No. 1996, 7 Pgs. Anaheim, CA.

Karp, et al., Abstract No. 156 From proceedings of the 41st Annual Meeting, Scientific Papers, vol. 35, No. 5, Attenuation Correction in Pet using a Singles Transmission Source, May 1994, p. 41P.

G. Muehllehner, et al. Abstract No. 284, From proceedings of the 42nd Annual Meeting, Scientific Papers, Spect Scanner with Pet Coincidence Capability, *Journal of Nuclear Medicine,* Jun. 14, 1995, p. 70P.

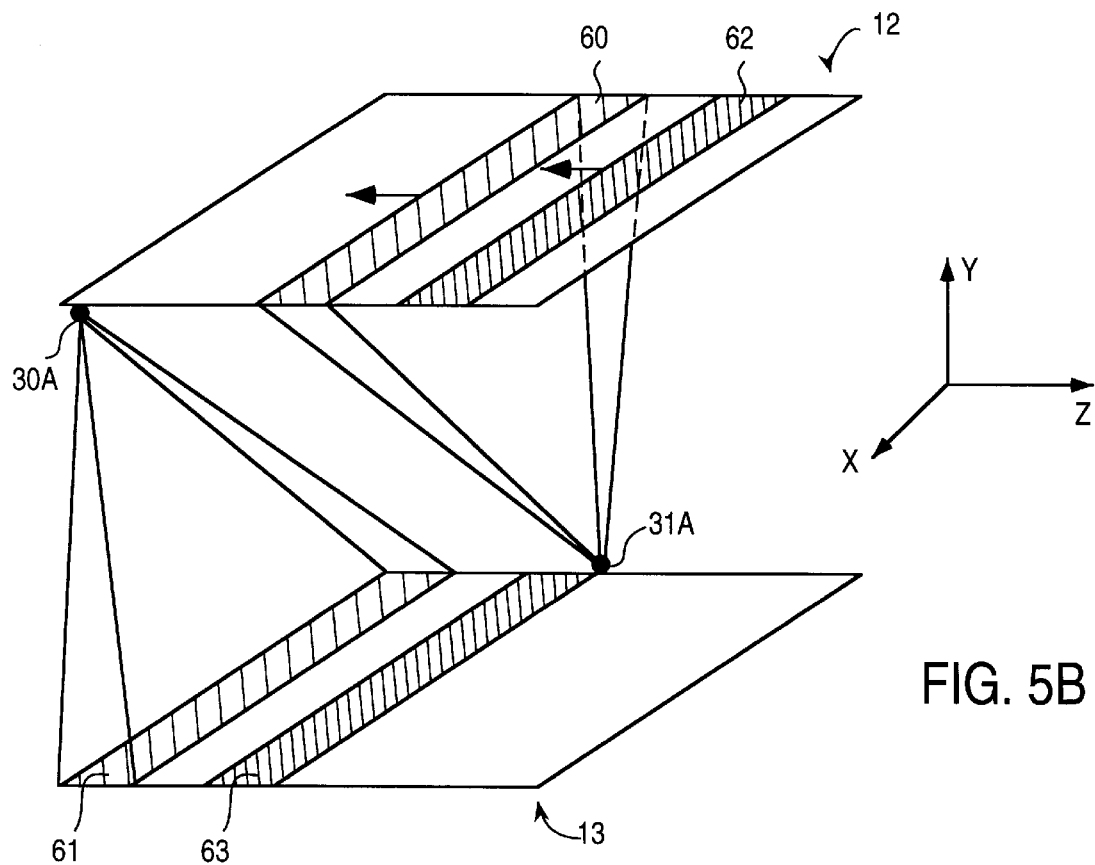
FIG. 5B
FIG. 6
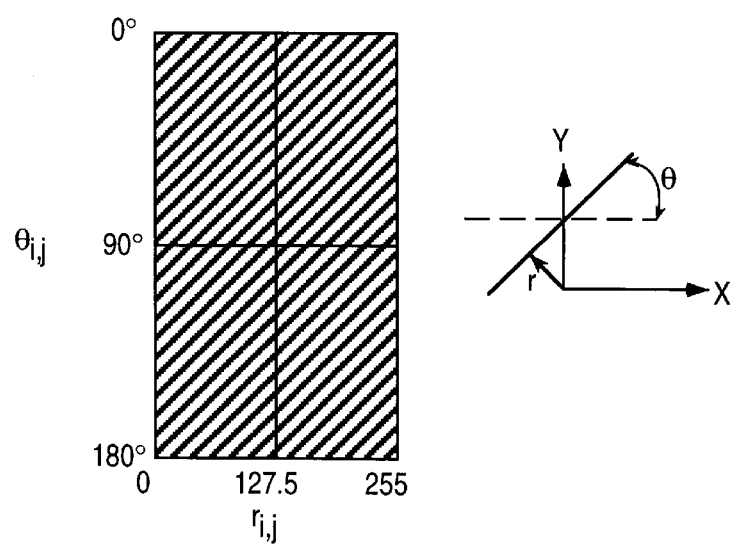

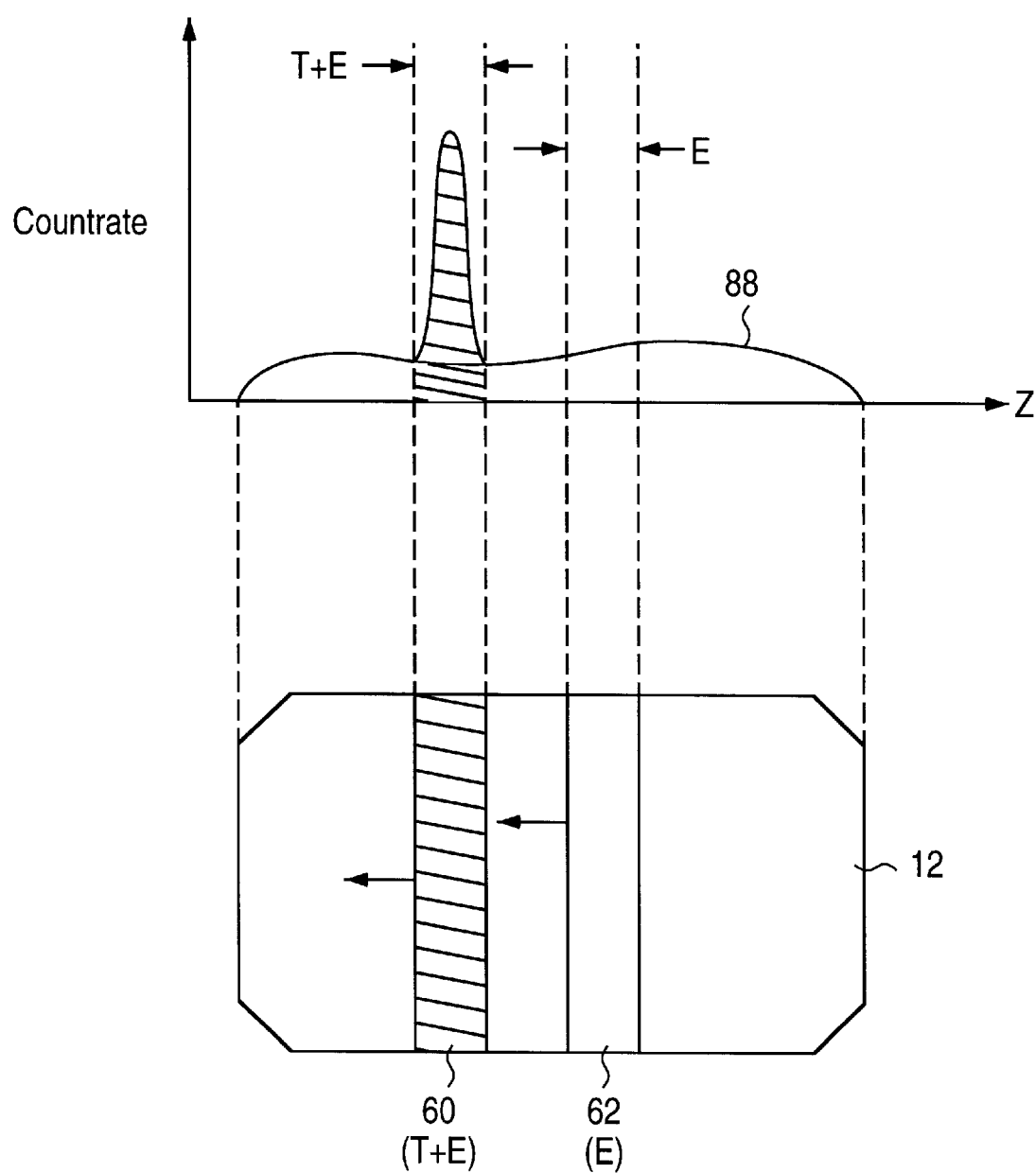

DUAL-MODE GAMMA CAMERA SYSTEM UTILIZING SINGLE-PHOTON TRANSMISSION SCANNING FOR ATTENUATION CORRECTION OF PET DATA

FIELD OF THE INVENTION

The present invention pertains to the field of medical imaging. More particularly, the present invention relates to attenuation correction in nuclear medicine imaging systems.

BACKGROUND OF THE INVENTION

Two well-known medical imaging techniques in nuclear medicine are Single-Photon Emission Computed Tomography (SPECT) and Positron Emission Tomography (PET). Both techniques generally makes use of gamma cameras, which detect gamma rays emitted from within the patient's body after the patient has been injected with a radiopharmaceutical substance, and a computer system, which processes the acquired data to generate images of internal structures or functions of the body. However, SPECT imaging is based on the detection of individual gamma rays emitted from the body, while PET imaging is based on the detection of gamma ray pairs that are emitted in coincidence in opposite directions due to electron-positron annihilations. PET imaging is therefore often referred to as "coincidence" imaging. Although past gamma camera systems have generally been either dedicated PET systems or dedicated SPECT systems, it is desirable to have a system that is capable of both SPECT and PET imaging. Many dedicated PET systems consist of a fixed array of detectors which partially or completely surround the patient. Such systems tend to be more expensive and less flexible, however, than systems which employ multiple detector "heads" that can be rotated about the patient. Therefore, it is further desirable to have dual SPECT/PET gamma camera imaging system which has multiple rotatable detector heads, rather than a fixed array of detectors.

One factor which has a significant impact on image quality in nuclear medicine is non-uniform attenuation. Non-uniform attenuation refers to the attenuation of radiation emitted from an organ of interest before the radiation can be detected, which tends to degrade image quality. One technique which has been used to correct for nonuniform attenuation is transmission scanning, in which gamma radiation from a known source is transmitted through the patient to a corresponding scintillation detector and used to form a transmission image. The transmission images provide an indication of the amount attenuation caused by various structures of the body and can thereby be used to correct for attenuation in the emission images. For purposes of performing attenuation correction on PET images, such transmission scans have commonly been implemented using coincidence transmission sources. However, for various reasons it may be desirable to perform a transmission scan for PET using a single-photon ("singles") source. See, e.g., S. K. Yu et al., "Single Photon Transmission Measurements in Positron Emission Tomography Using $^{137}$Cs," Phys. Med. Biol., vol. 40, 1995, and R. A. deKemp, "Attenuation Correction in Positron Emission Tomography Using Single Photon Transmission Measurement," McMaster University, Hamilton, Ontario, Canada, September 1992. Coincidence events generally represent only a small fraction of the total detected events during an imaging session. Consequently, a singles transmission source may be preferable because of its higher associated countrate in comparison to a coincidence source. A higher countrate tends to provide a higher signal-to-noise ratio than a lower countrate does. Also, at higher source strengths, a singles source may result in higher counting efficiency because of the higher deadtime losses that are often associated with a coincidence source (i.e., from too much activity at the detector nearest to the source).

Thus, it is desirable to provide a dual SPECT/PET gamma camera imaging system which has multiple rotatable detectors and which provides attenuation correction for PET based on transmission scanning with a singles transmission source.

SUMMARY OF THE INVENTION

The present invention includes a nuclear camera system which comprises a number of detectors for detecting radiation emitted from an object, a single-photon radiation source for transmitting radiation through the object to a particular detector, and a gantry supporting the detectors and the radiation source. The gantry provides rotation of the detectors and the radiation source about an axis of rotation, such that the angular position of the radiation source about the axis of rotation is fixed relative to the angular position of the particular detector to which it transmits. The camera system further includes a selection unit coupled to the detectors which allows either a single-photon mode or a coincidence mode to be selected and which configures the detectors for acquisition of data according to the selection. The camera system further includes a processing system coupled to control the detectors and the radiation source. The processing system controls the detectors to acquire coincidence emission data of the object. The processing system further controls the radiation source to acquire transmission data of the object and corrects the coincidence emission data using the transmission data. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which:

FIG. 5B illustrates two axially offset radiation point sources illuminating two corresponding detector imaging surfaces using fanbeam illumination profiles.

FIG. 6 illustrates an example of a sinogram which may be obtained using the configuration of FIGS. 5A with only one detector operating.

FIG. 11A illustrates countrate as function of position along the detector imaging surface and the spatial windowing for transmission (T+E) and contamination (E) events.

DETAILED DESCRIPTION

A dual-mode gamma camera system which utilizes single-photon transmission scanning to provide attenuation correction of PET data is described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to facilitate description of the present invention.

Figure 1:
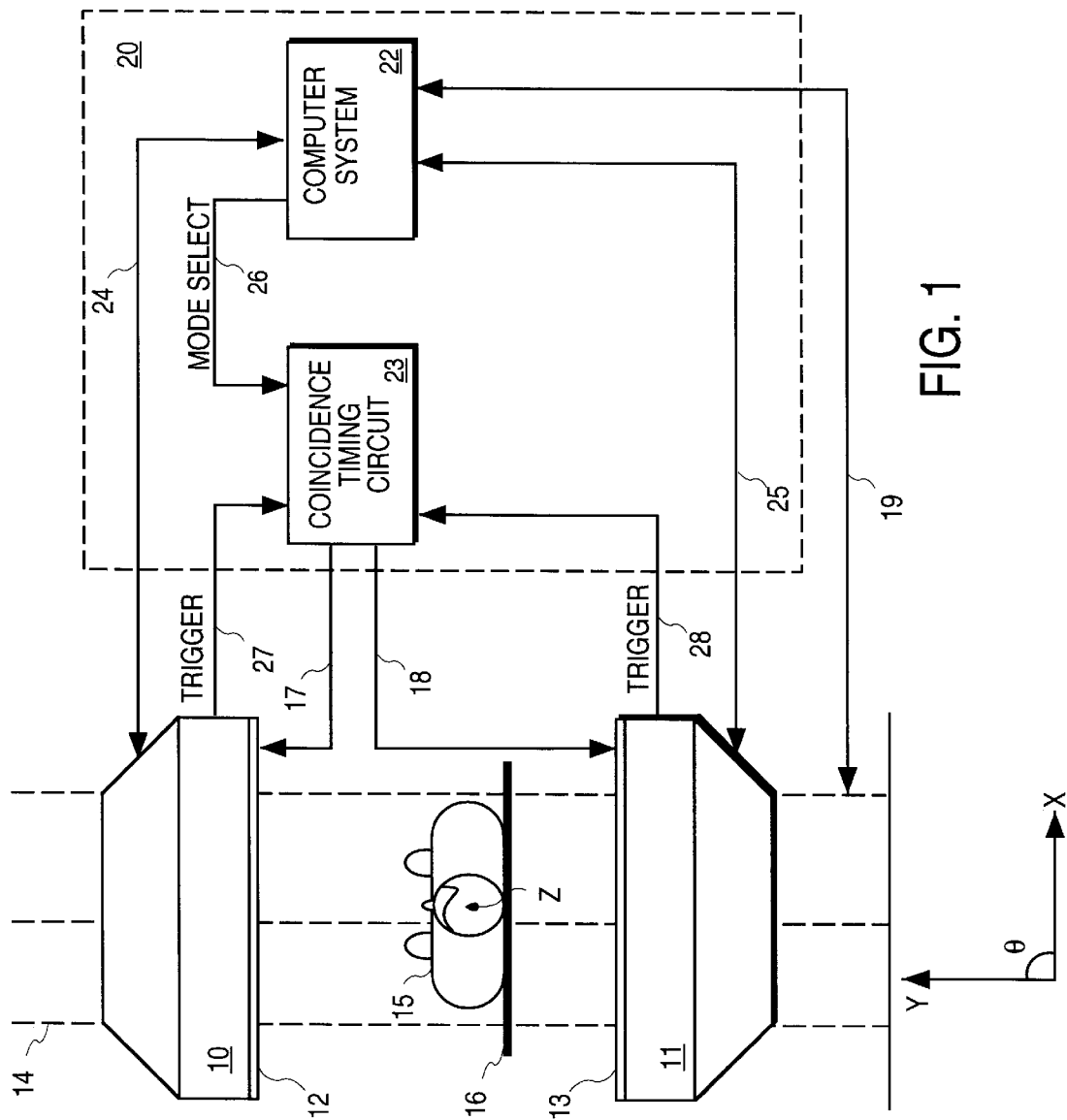
FIG. 1 is a block diagram of a dual PET/SPECT gamma camera system.

Certain aspects of the present invention relate to attenuation correction of PET images in a dual-detector gamma camera system capable of both SPECT and PET imaging. An example of such a system is illustrated in FIG. 1 in block diagram form. A gamma camera system having dual SPECT/PET capability is described in detail in U.S. Pat. No. 5,585,637 and U.S. Pat. No. 5,608,221, both issued to Bertelsen et al. Certain aspects of such capability are described below as background information. In addition, although the following description relates to an embodiment of the present invention having two gamma camera detectors, the present invention is not limited to two-detector system.

The dual-mode gamma camera system 1 of FIG. 1 includes a processing system 20 coupled to a pair of scintillation detectors 10 and 11. The detectors 10 and 11 have imaging surfaces 12 and 13, respectively. The detectors 10 and 11 are mounted on a gantry 14, which can rotate the detectors 10 and 11 either individually or in unison about an axis of rotation, z (the "axis"), which is perpendicular to the x-y plane. A patient 15 to be imaged rests on a table 16 between the detectors 10 and 11. The detectors are shown configured in a 180 degree orientation (i.e., offset 180 degrees relative to each other about the axis of rotation) to facilitate coincidence (PET) imaging. Generally, the processing system 20 controls the gantry 14 to provide movement of the detectors 10 and 11, controls the mode (PET vs. SPECT) of the detectors 10 and 11, receives data acquired by the detectors 10 and 11, and generates images from that data. Each of the detectors 10 and 11 includes a scintillation crystal, an array of photomultiplier tubes (PMTs) arranged in a conventional two dimensional matrix, and various processing circuitry. Gamma camera detectors such as detectors 10 and 11 are well-known in the art; accordingly a detailed description of the internal components of detectors 10 and 11 and their operation is not necessary to an understanding of the present invention and is not provided herein. The scintillation crystals can be composed of sodium iodine (NaI) and may be located between a collimator (not shown) and the PMT array.

The processing system 20 includes a programmable coincidence timing circuit (CTC) 23 coupled to the detectors 10 and 11 and coupled to a computer system 22. Note that in other embodiments, a CTC 23 may be included in one or both of the detectors 10 and 11. The computer system 22 may include a conventional, general purpose workstation, a single-board computer, or personal computer (PC). A signal 26 from the computer system 22 indicates to the CTC 23 the current mode of operation (i.e., SPECT or PET). Upon detection of a scintillation event in either detector 10 or 11, lines 27 and 28, respectively, carry trigger pulses to CTC 23. CTC unit 23 then generates valid event trigger signals over lines 17 and 18 for the detectors 10 and 11, respectively, according to the selected mode of operation (SPECT or PET). The valid event trigger signals 17 and 18 are used by the detectors 10 and 11 to start (or reset) their accumulators (integrators), which accumulate (integrate) the energy of detected scintillation events and are therefore called "valid event" trigger signals. In the PET mode, integration is not started until a coincidence is detected between detector 10 and 11. In SPECT mode, an integration is started for each detector upon a trigger event, regardless of coincidence. After integration and centroiding, the detectors 10 and 11 output over lines 24 and 25, respectively, X and Y position values and Z energy values.

Figure 2:
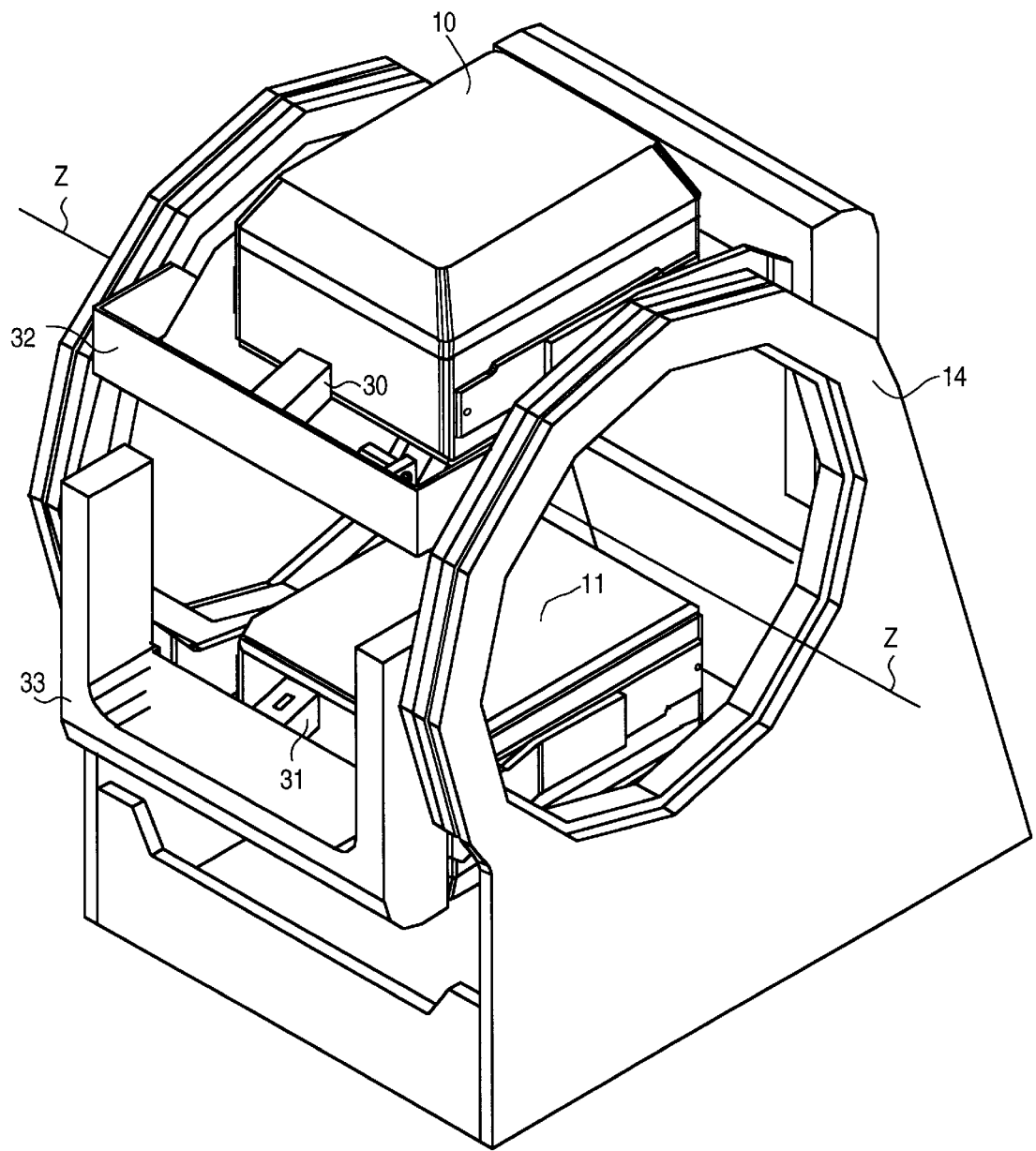
FIG. 2 is a perspective view of the gantry and detectors of the gamma camera system of FIG. 1.

FIG. 2 illustrates a perspective view of the gantry 14 and detectors 10 and 11, according to one embodiment. FIG. 2 also shows two transmission source assemblies 30 and 31 for performing transmission scans. As will be described below, each of the transmission source assemblies 30 and 31 includes a single-photon ("singles") mode radiation source used to perform transmission scans for correcting PET images for the effects of attenuation. In one embodiment, each of the source assemblies 30 and 31 includes a $Cs^{137}$ point source. As will be described below, each of the source assemblies 30 and 31 includes appropriate shielding as well as collimation designed to provide a specific illumination profile. Source assembly 30 is mounted to a track assembly 32 adjacent to detector 10 and outside the field of view (FOV) of detector 10. Source assembly 30 has an aperture and is mounted so that the aperture faces detector 11 to allow radiation from source assembly 30 to illuminate detector 11. Similarly, source assembly 31 is mounted to a track assembly 33 adjacent to detector 11 and outside the FOV of detector 11. Source assembly 31 further has an aperture and is mounted so that the aperture faces detector 10 to allow radiation from source assembly 31 to illuminate detector 10. Track assemblies 32 and 33 provide a mechanism for translating the source assemblies along the z axis in one embodiment of the present invention. Track assemblies 32 and 33 are rotatable about the z axis in unison with detectors 10 and 11; consequently, the point sources 30 and 31 at all times remain fixed relative to detectors 10 and 11 in terms of their angular positions about the z axis.

Figure 3:
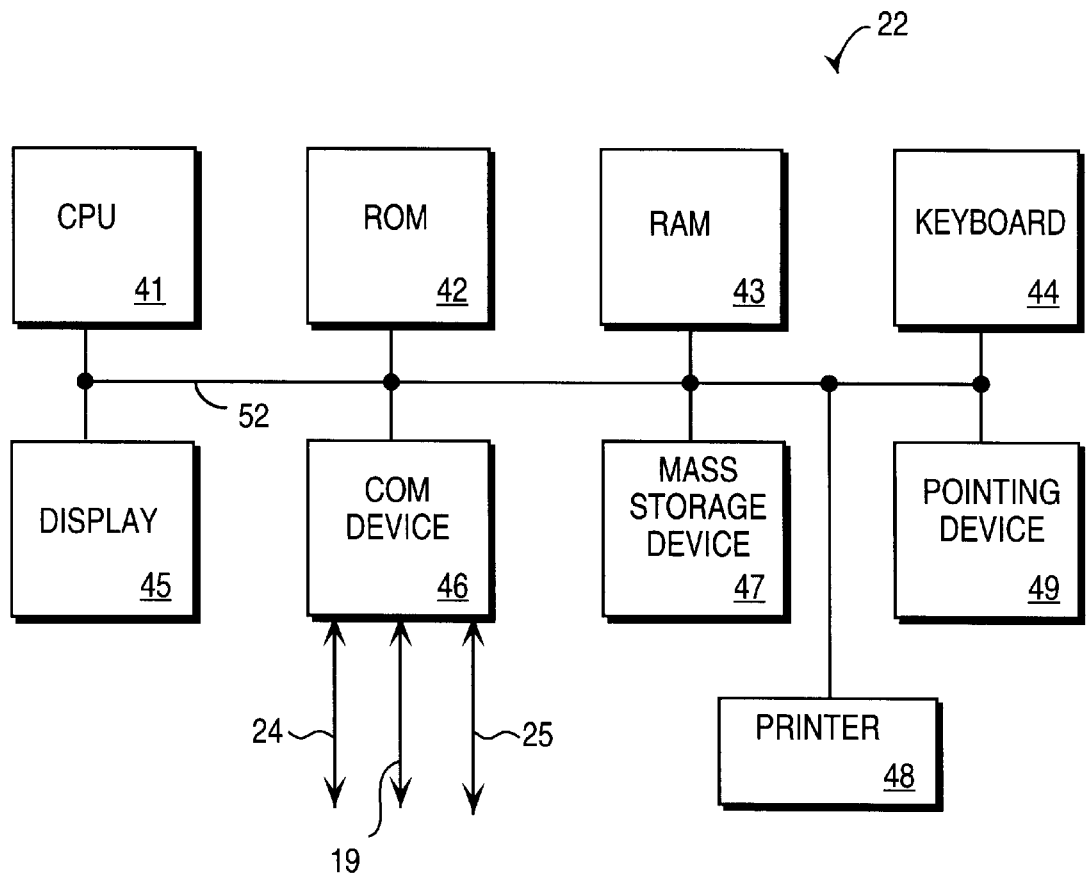
FIG. 3 is a block diagram of the computer system of the gamma camera system of FIG. 1.

FIG. 3 illustrates a block diagram of the computer system 22. The computer system 22 comprises one or more central processing units (CPU) 41, a read-only memory (ROM) 42, and a random access memory (RAM) 43, each coupled to a bus 52 for communicating information within the system 22.

Note that the bus 52 may comprise multiple physical buses coupled together by various bridges, controllers, and/or adapters. Also coupled to the bus 52 are a mass storage device 47, such as a magnetic or optical disk and disk drive; a display device 45, such as a cathode ray tube (CRT) or liquid crystal display (LCD); an alphanumeric keyboard 44; a pointing device 49, such as a mouse, trackball, or touchpad; and, a communication device 46. The communication device 46 includes a high speed communication port for communicating with the gantry 14 and detectors 10 and 11 via signals 19, 24 and 25.

The computer system 22 executes software instructions to implement procedures according to the present invention and various other functions. Specifically, the CPU 41 may be configured to perform certain steps in accordance with the present invention by software instructions stored in RAM 43, ROM 42, mass storage device 47, or a combination of these devices.

Figure 4:
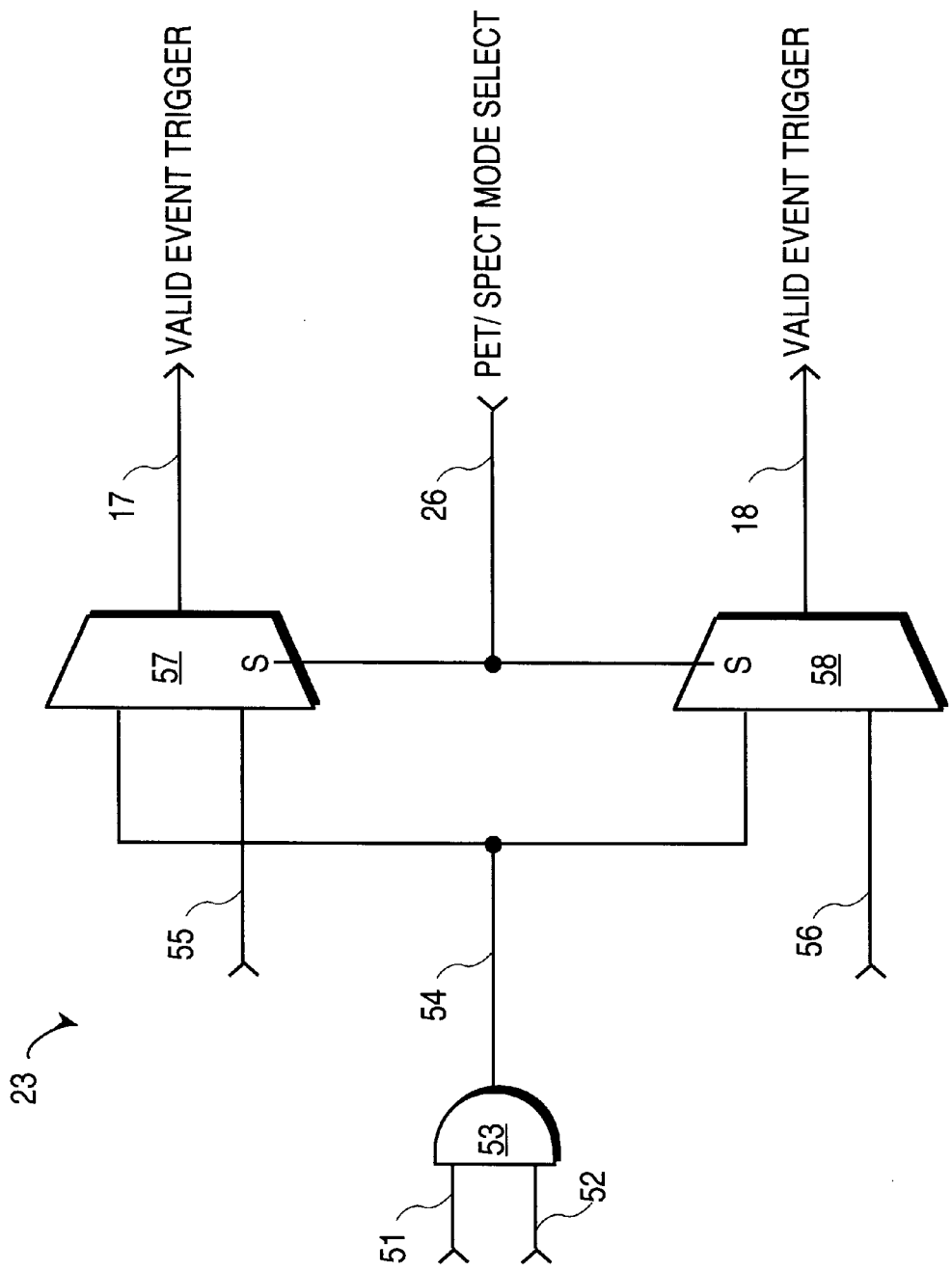
FIG. 4 illustrates a coincidence timing circuit for switching between PET and SPECT modes.

As noted above, the CTC 23 (see FIG. 1) is used to control the operational mode (SPECT or PET) of the gamma camera system 1. FIG. 4 illustrates one embodiment of the CTC 23 in greater detail. FIG. 4 shows four signals, 51, 52, 55, and 56. Signals 51 and 55 are trigger signals generated by detector 10 in response to scintillation events and are provided to CTC 23 over line 27. Signal 55 is generated by SPECT detection electronics in detector 10, and signal 51 is generated by PET detection electronics in detector 10. Signals 52 and 56 are trigger signals generated by detector 11 in response to scintillation events and are provided to CTC 23 over line 28. Signal 56 is generated by SPECT detection electronics in detector 11 while signal 52 is generated by PET detection electronics in detectors 11. Signals 51 and 52 from the PET detection electronics of detectors 10 and 11, respectively, are provided as inputs to an AND gate 53. AND gate 53 outputs a signal 54, which is asserted only if signals 51 and 52 are in coincidence (i.e., both asserted within a predetermined time window). The CTC 23 also includes two double-input multiplexors 57 and 58. Multiplexor 57 receives as input signal 55 from the SPECT detection electronics of detector 10 and signal 54 from AND gate 53. Multiplexor 58 receives as input signal 56 from the SPECT detection electronics of detector 11 and signal 54 from AND gate 53.

A mode selection control signal 26 is coupled to the select inputs of multiplexors 57 and 58. The control signal 26 is used to switch between PET and SPECT modes of operation. The control signal 26 may result from a command entered by a user through a user interface provided by the computer system 22. When the control signal 26 has a value indicating PET mode is desired, then an asserted signal over line 54 passes over both line 17 to detector 10 and over line 18 to detector 11 as valid event trigger signals.

When the control signal 26 has a value indicating SPECT mode is desired, then the signal over line 55 is carried over line 17 to detector 10, and the signal over line 56 is carried over line 18 to detector 11 as valid event trigger signals.

Signals over line 17 are used to trigger event integrators in the detection circuitry of detector 10, and signals over line 18 are used to trigger event integrators in the detection circuitry of detector 11.

Singles-Mode Fanbeam Transmission Scan

Figure 5A:
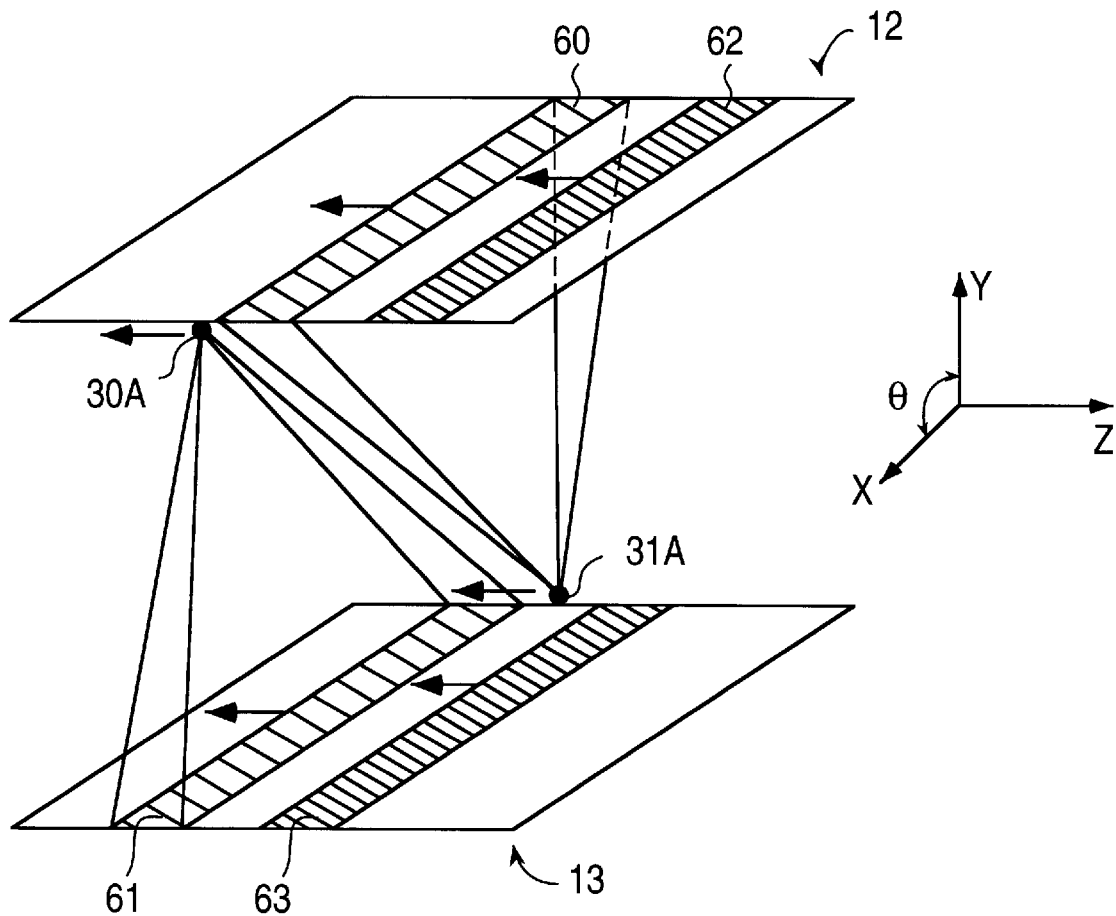
FIG. 5A illustrates two radiation point sources illuminating two corresponding detector imaging surfaces using fanbeam illumination profiles.

The present invention includes the use of two singles-mode radiation point sources to perform a transmission scan for purposes of performing attenuation correction on coincidence (PET) data. In one embodiment, each of the point sources is a $Cs^{137}$ source having an energy peak at 662 keV. In the embodiment of FIG. 2, source assemblies 30 and 31 are mounted on the same side of the detectors 10 and 11 in the transaxial (x) direction. FIGS. 5A and 5B illustrate an alternative embodiment in which the source assemblies 30 and 31 are mounted on opposite sides of detectors 10 and 11 in the transaxial direction. Referring now to FIG. 5A, source assemblies 30 and 31 (not shown) contain $Cs^{137}$ point sources 30A and 31A, respectively. Point source 30A is mounted adjacent to the imaging surface 12 of detector 10, while point source 31A is mounted adjacent to the imaging surface 13 of detector 11. As indicated above, the point sources 30A and 31A remain fixed relative to detectors 10 and 11 in terms of their angular positions about the z axis.

Transmission detection (spatial) windows 60 and 61 are defined on the imaging surfaces 12 and 13 of detectors 10 and 11, respectively, for detecting transmission radiation transmitted from sources 31A and 30A, respectively. The transmission detection windows 60 and 61 are defined electronically by the detectors and/or the computer system 22 in a manner that is well-known in the art. The transmission detection windows 60 and 61 are defined for detection of photons within an energy range centered at 662 keV. Transmission detection window 60 is aligned with source 31A relative to the z axis ("axially"), and transmission detection windows 61 is defined so that it is aligned axially with source 30A. In the embodiment of FIG. 5A, the point sources 30A and 31A are offset axially by an amount that is small relative to the axial field of view (FOV) of detectors 10 and 11, such that transmission detection windows 60 and 61 are substantially adjacent in the z direction. This offset reduces transmission self-contamination (i.e., the undesirable detection of transmission radiation by the detector nearest to the transmitting source), which is discussed further below.

Also defined on the imaging surfaces 12 and 13 are emission contamination detection windows 62 and 63, respectively. The emission contamination detection windows 62 and 63 are used for purposes of correcting for emission contamination of the transmission scan, as will be described below.

During transmission scanning, the point sources 30A and 31A are scanned synchronously across the FOVs of detectors 10 and 11 along the z axis under the control of the processing system 20. Further, transmission detection windows 60 and 61 are scanned synchronously with their corresponding point sources, 31A and 30A. Only radiation detected within transmission detection windows 60 and 61 is recognized for purposes of acquiring a transmission data set (i.e., projection). In addition, each of the source assemblies 30 and 31 (see in FIG. 2) includes collimation designed to produce a fanbeam illumination profile, as shown in FIG. 5A, to substantially limit transmission radiation to transmission detection windows 60 and 61, respectively.

It may be desirable to have a greater axial offset between the point sources 30A and 31A than that shown in FIG. 5A.

Accordingly, FIG. 5B illustrates an alternative embodiment having a greater offset. A larger axial offset between the point sources 30A and 31A may further reduce transmission self-contamination as well as cross-scatter of transmission radiation into the wrong detection window.

During a PET imaging session, the detectors 10 and 11 are arranged in a 180° orientation, and are used to detect emission radiation from a number of angular positions about the z axis. Accordingly, at each of these angular positions about the z axis, a transmission scan is performed by scanning the transmission radiation fanbeams and the corresponding transmission detection windows 60 and 61 axially across the FOVs of the detectors 10 and 11. Scanning of the fanbeams may be accomplished by translating the source assemblies 30 and 31 axially.

In an alternative embodiment, scanning can be performed by maintaining the point sources in a fixed position along the z axis and using a rotating aperture to scan the fanbeam across the FOV of the opposing detector.

In such an embodiment, the count density at the corresponding detector will vary depending upon the inclination angle of the fanbeam. For example, the count density will tend to decrease as the distance between the source and the illuminated portion of the detector increases and, consequently, the illuminated area on the detector increases. However, assuming the camera system is calibrated using a blank transmission scan (i.e., no object in the field of view), as is conventional practice in nuclear imaging, these effects will be normalized out when the actual images are generated.

In yet another embodiment, the transmission scan may be performed by maintaining fixed axial (z) positions of the sources 30A and 31A while each of the sources 30A and 31A illuminates the entire imaging surface of the corresponding detector, rather than scanning a radiation beam across the imaging surface. In this embodiment, a single-slice rebinning algorithm may be adequate if the effective axial field of view is sufficiently small, such that the incident angle at which the transmission radiation impinges upon the detector surface is close to 90 degrees. However, if the axial field of view to be scanned is relatively large, such that the incident angle becomes more acute, it may be desirable to use a three-dimensional rebinning algorithm. An example of a three-dimensional rebinning algorithm which may be used is the Fourier rebinning technique, which is described by M. Defrise et al., "Exact and Approximate Rebinning Algorithms for 3-D PET Data," IEEE Transactions on Medical Imaging, vol. 16, No. 2, April 1997.

The geometry illustrated in FIGS. 5A results in a base pattern sinogram similar to that illustrated in FIG. 6 (for one detector) for 32 angular stops over 360° of rotation of the detectors and point sources. In FIG. 6, the diagonal lines regions represent regions of sinogram space in which data is acquired, while the gaps between the lines represent regions in which there is no coverage. This effect occurs when the sinogram is generated by taking all of the possible 1024 different transverse positions that a detector can produce and then calculating the corresponding r and θ. Such gaps in the sinogram may produce artifacts in the reconstructed images.

Therefore, it may be desirable for the rebinning software to circumvent this effect. A solution is to store raw detector coordinates and, during post-processing, fill in the sinogram by searching for and interpolating amongst the possible raw image (projection) locations that could have contributed to a particular point in the sinogram.

Figure 7:
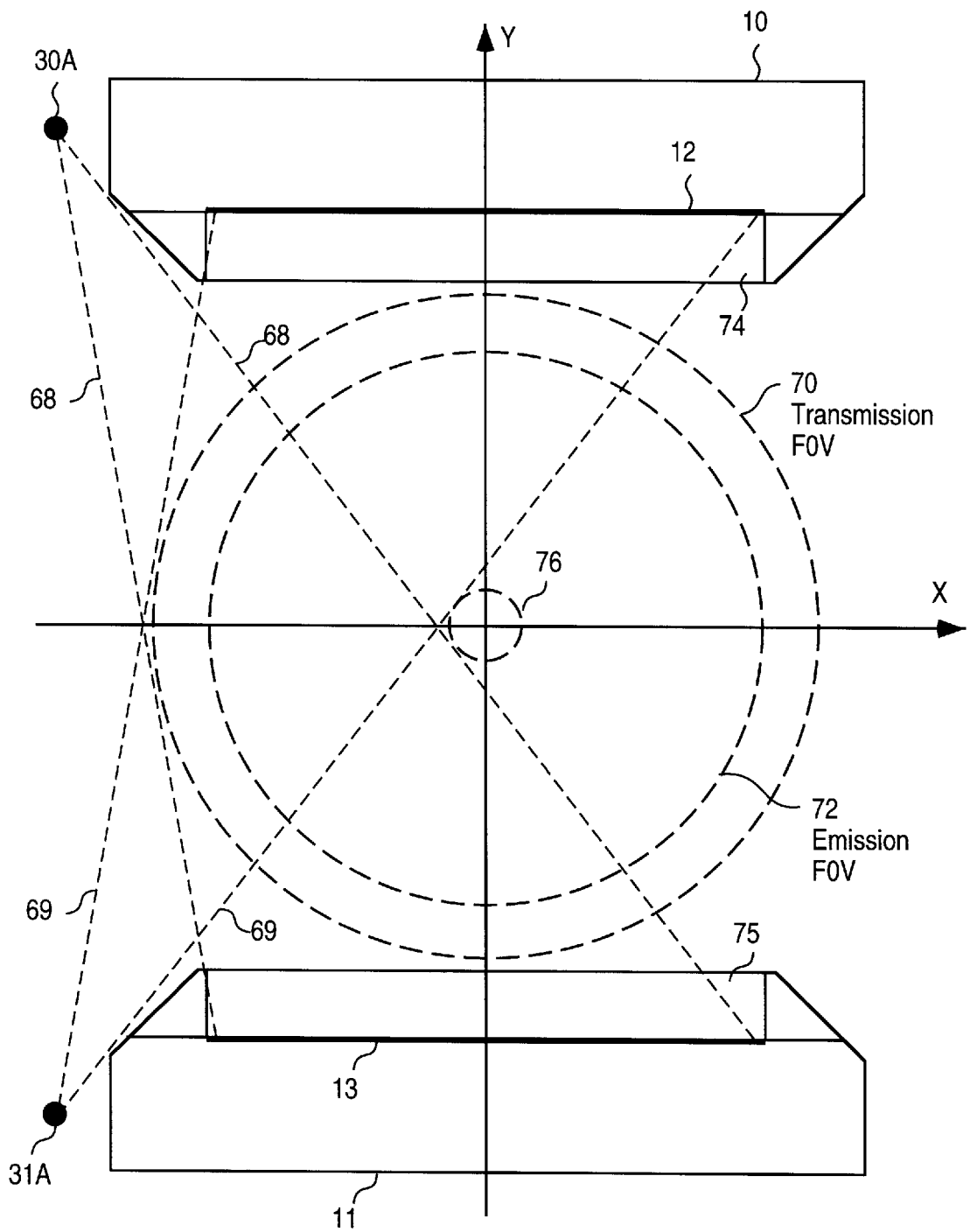
FIG. 7 illustrates an axial view of radiation point sources and detectors in relation to the fields of view of the detectors.

FIG. 7 illustrates the geometry associated with the transmission scanning of the present invention in terms of the FOVs of the detectors 10 and 11 for one embodiment. Specifically, FIG. 7 illustrates a view in a transverse (x-y) plane according to an embodiment in which the sources 30A and 31A are on the same side of detectors 10 and 11 in the transaxial (x) direction. In FIG. 7, septa 74 and 75 are disposed along the imaging surfaces 12 and 13 of detectors 10 and 11, respectively. Point sources 30A and 31A are mounted outside the FOVs of detectors 10 and 11. Such mounting avoids blocking the detectors and reduces transmission self-contamination. As noted above, a transmission scan across the entire axial width of detectors 10 and 11 is performed at each angular stop about the z axis. The aggregate effect of these transmission scans with the illustrated placement of point sources is a transmission FOV (in each transverse slice) represented by circle 70. The emission field of view (in each transverse slice) is represented by circle 72.

In one embodiment, the point sources 30A and 31A are mounted outside the FOVs of detectors 10 and 11, such that the detectors themselves limit the allowable beamwidth (in the transverse plane) of the fanbeams generated by sources 30A and 31A. In such an embodiment, the transmission FOV 70 is defined by two boundaries, an outside boundary and an inside boundary. The outside boundary is defined by the outer edges of the transmission fanbeams 68 and 69 at each of the angular stops about the z axis, while the inside boundary is defined by the circumference of circle 76. Thus, circle 76 represents a gap, or blind spot, in the transmission field of view 70. In order to prevent this gap from resulting in incomplete data acquisition, the computer system 22 causes the table 16 (FIG. 1) to move vertically and horizontally relative to the z axis in dependence on the angular positions of the detectors 10 and 11 about the z axis in order to provide full coverage of the object of interest. Such table motion effectively increases the transmission FOV 70. In one embodiment, table motion is controlled by the gantry 14, which includes a dedicated microprocessor (not shown). A technique for providing table motion in a medical imaging system is described in U.S. Pat. No. 5,444,252 of Hug et al., which is assigned to the assignee of the present invention.

Figure 8A:
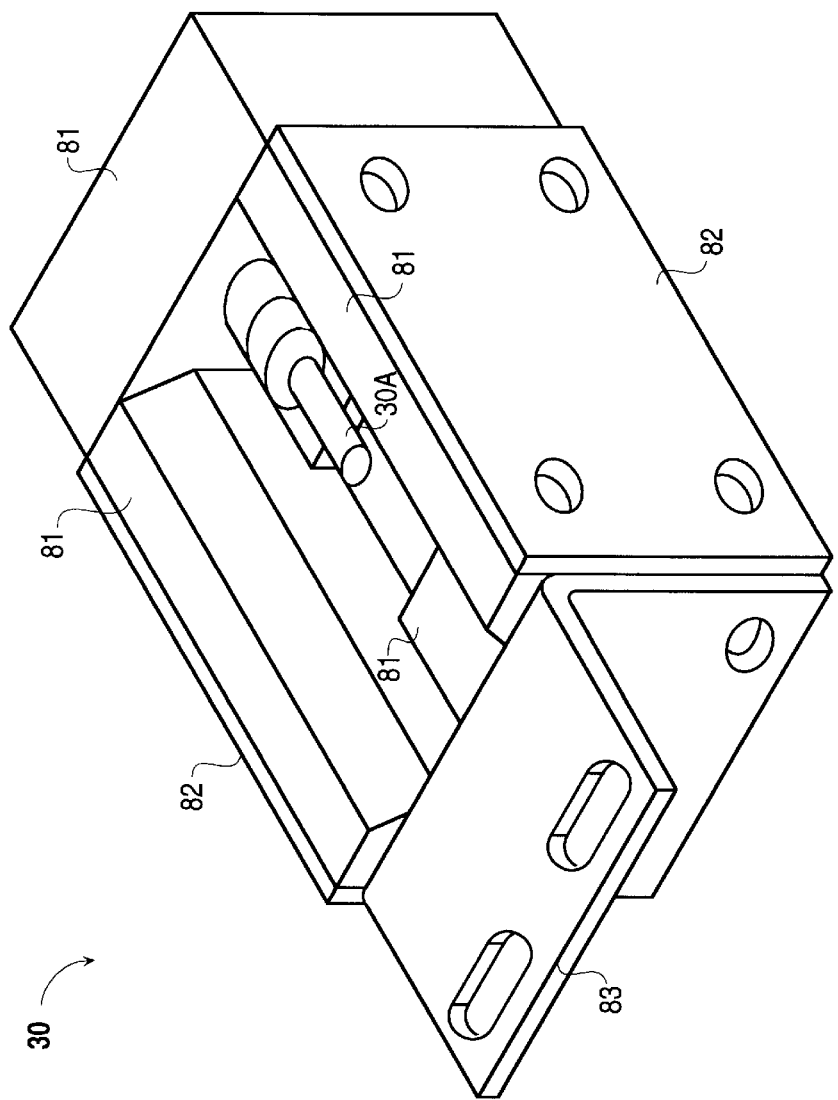
FIG. 8A illustrates a radiation point source assembly.

FIG. 8A illustrates the point source assembly 30 according to one embodiment. It should be noted that point source assembly 31 is substantially identical to point source assembly 30 unless specifically stated otherwise. The assembly 30 includes a number of lead shielding structures 81, which partially enclose the point source 30A. The lead structures 81 are encased by aluminum or steel brackets 82 and 83. Bracket 83 forms a means for mounting source assembly 30 to track assembly 32 (see FIG. 2) to allow axial translation of source assembly 30.

Figure 8B:
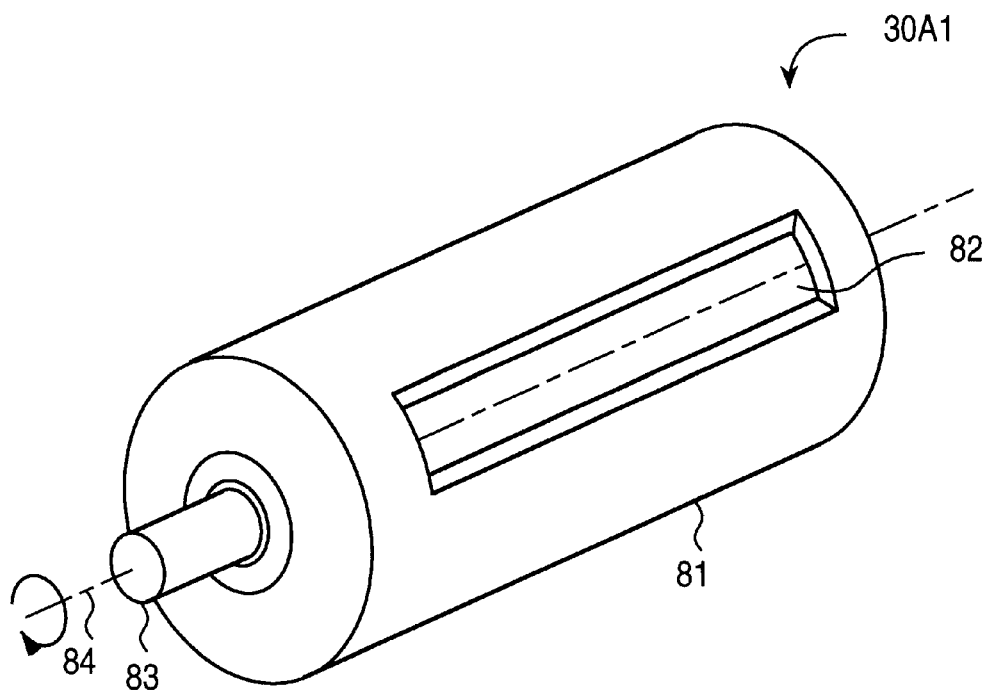
FIG. 8B illustrates a radiation point source assembly according to an embodiment using a rotating aperture.

FIG. 8B shows an alternative embodiment of a point source assembly or use in an embodiment in which the point sources are not translated along the z axis in order to provide the scanning of the fanbeam. The source assembly 30A1 is fixed axially but includes an aperture 82 that is rotated about an axis 84 to provide the scanning of the fanbeam. The source assembly 30A1 is mounted appropriately to the gantry 14 with axis 84 is parallel to the x axis. The point source in this embodiment (not shown) is encased with appropriate shielding 81 similar to that of assembly 30A in FIG. 8A. The casing 81 and aperture 82 are rotated about a shaft 83 (i.e., about axis 84).

Figure 9A:
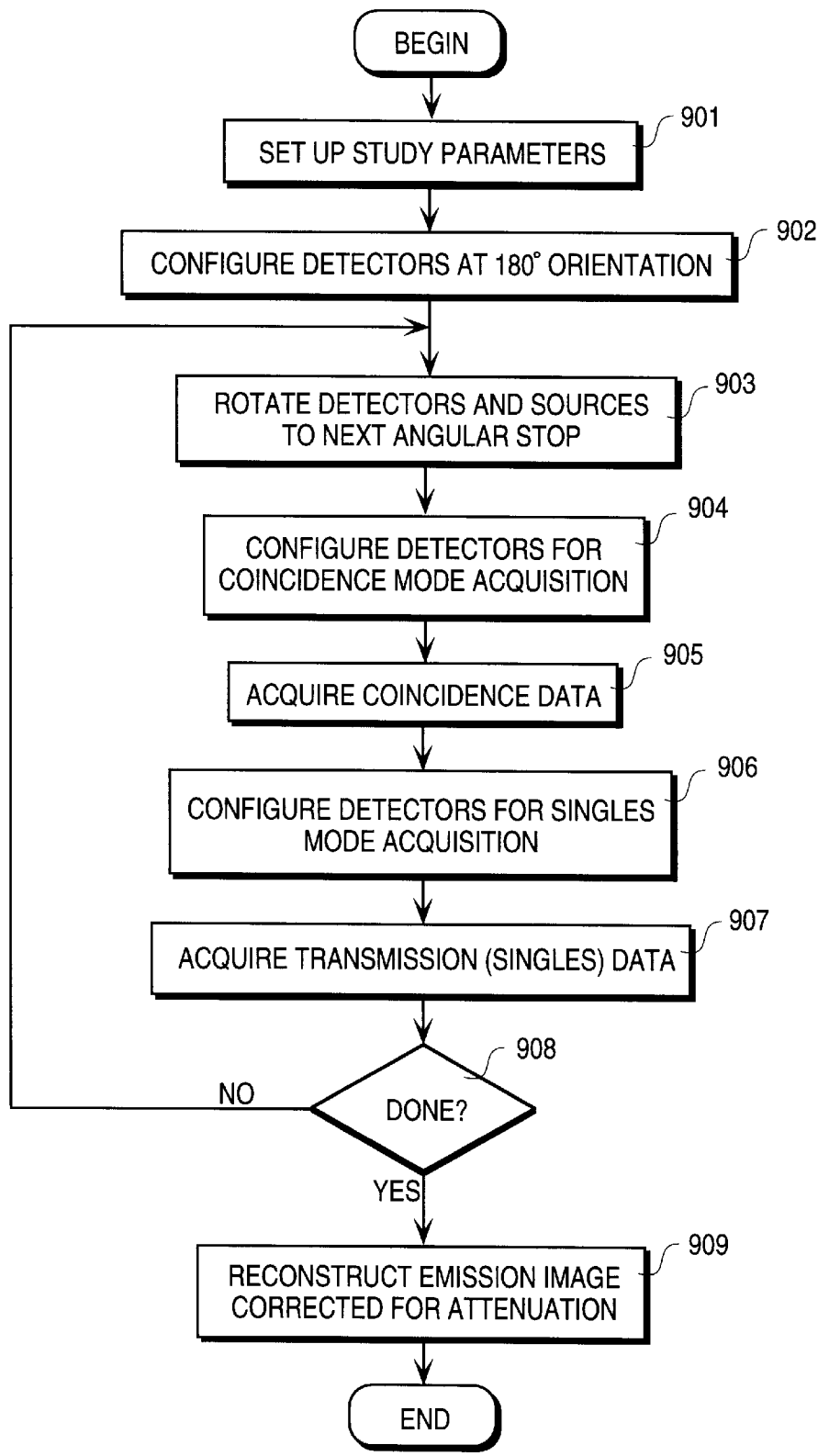
FIGS. 9A and 9B are flow diagrams illustrating overall routines for generating attenuation corrected PET images according to two different embodiments.

FIG. 9A illustrates an overall routine according to one embodiment for acquiring both coincidence (emission) data for a PET study, as well as singles transmission data for attenuation correction of the coincidence data. In step 901, the initial study parameters are set up in the computer system 22. These parameters include, for example, the total number of angular stops about the z axis and the total acquisition time at each stop for both the emission scan and transmission scan. Next, in step 902, the detectors 10 and 11 are configured in a 180° orientation about the z axis to enable coincidence detection. In step 903 the detectors 10 and 11 are rotated (together with source assemblies 30 and 31) to the first (or next) angular stop about the z axis. In step 904, the detectors are configured for detection of emission data in coincidence mode. After acquiring coincidence data for the prescribed time period in step 905, the detectors are then configured for detection in the singles mode in step 906. Next, in step 907, a transmission scan is performed in the manner described above (i.e., by scanning the transmission radiation fanbeams across the detector imaging surfaces), and the transmission data is acquired as singles data. If there are additional angular stops at which data is to be acquired (step 908), then the routine repeats from step 903. Otherwise, in step 909 the emission image is reconstructed and corrected for attenuation using the transmission image data.

Figure 9B:
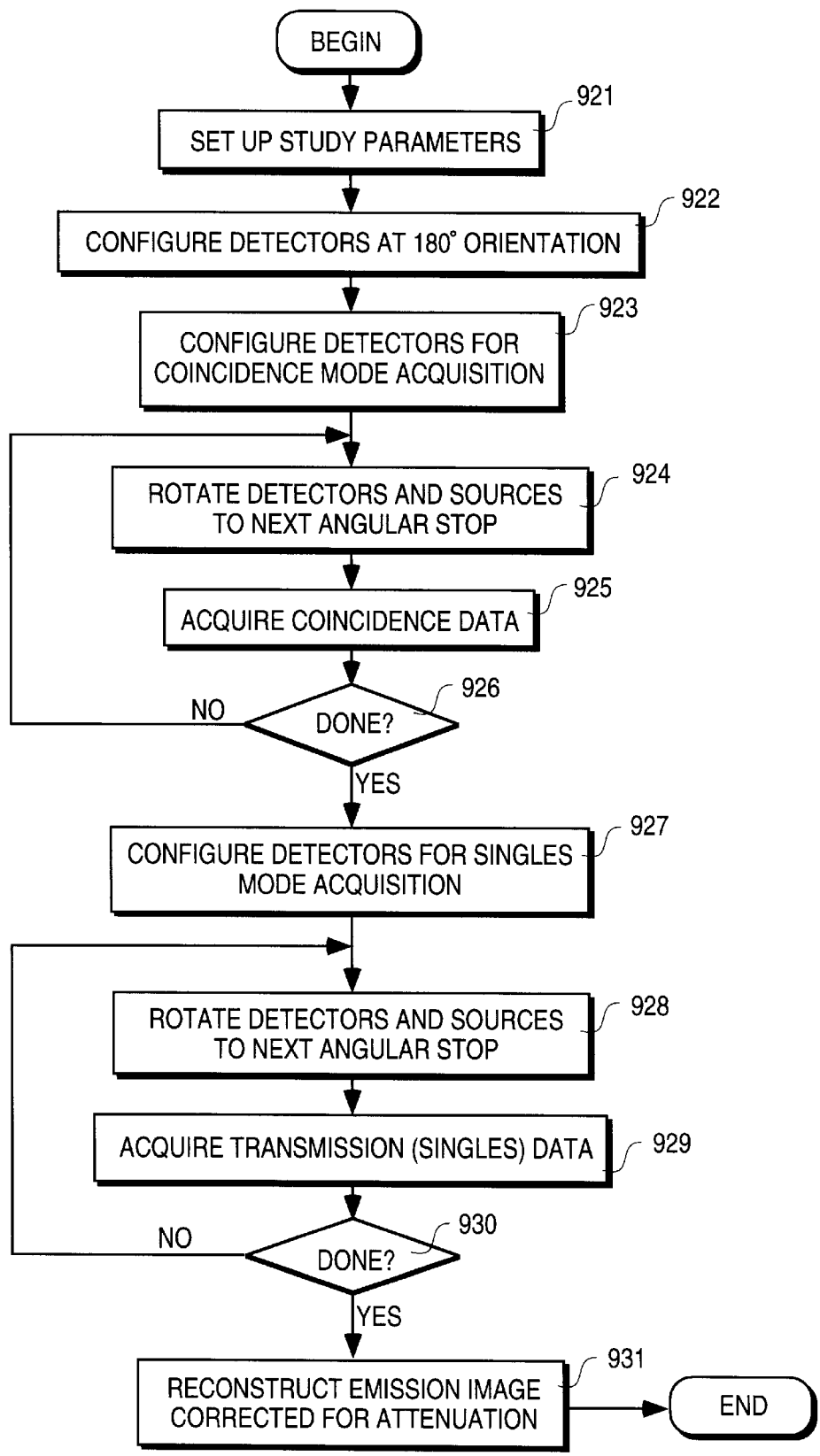

FIG. 9B illustrates another overall routine for acquiring both coincidence (emission) data for a PET study and transmission data for attenuation correction, according to a second embodiment. In the embodiment of FIG. 9B, the emission data is acquired first followed by acquisition of transmission data. More specifically, the study parameters are set up in step 921, and the detectors are configured in a 180 degree orientation in step 922. Next, after configuring the detectors for coincidence mode acquisition in step 923, emission data is acquired for the complete range of projection angles, rotating the detectors between angular stops about the z axis as required (steps 924, 925 and 926). After the emission data is acquired, the detectors are reconfigured for singles-mode acquisition in step 927, and transmission data is acquired for the complete range of projection angles, rotating the detectors between angular stops about the z axis as required (steps 928, 929 and 930). An emission image is then reconstructed and corrected for attenuation using the transmission image data in step 931.

Correction of Emission Contamination in the Transmission Scan

Figure 11B:
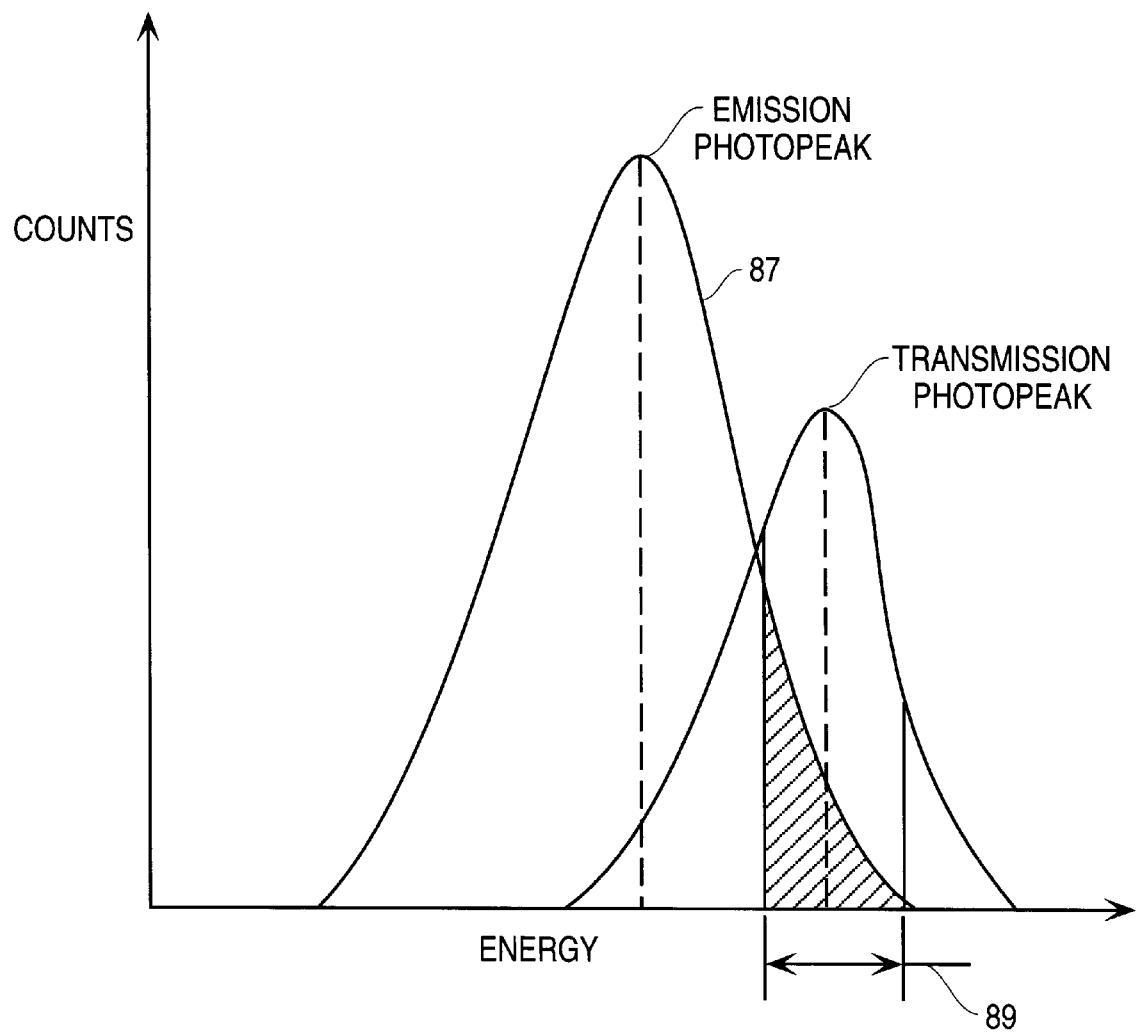
FIG. 11B illustrates a relationship between emission and transmission photopeaks for one embodiment.

If the transmission scan is performed after injection of the radionuclide into the patient, emission activity will be present during the transmission scan. Accordingly, some of the emission activity may be detected (undesirably) within transmission detection windows 60 and 61 (see FIGS. 5A and 5B). The effect of this emission contamination in the transmission detection scan is illustrated in FIG. 11A, which plots countrate as a function of axial (z) position along the imaging surface 12 of a detector. A baseline countrate 88 of emission activity exists across the entire imaging surface 12 of the detector. In addition, within the transmission detection window 60, there is additional countrate attributable to transmission radiation from the corresponding transmission source 31A (not shown in FIG. 11A). Energy discrimination as a means for distinguishing between emission activity and transmission activity becomes relatively ineffective if the emission source and transmission source have photopeaks that are close together (e.g., a $Cs^{137}$ singles transmission source with a photopeak at 662 keV and a Flouro Deoxy Glucose, or FDG, coincidence emission source with a photopeak at 511 keV). The reason energy discrimination becomes relatively ineffective is that, as illustrated in FIG. 11B, a portion of the emission energy distribution 87 will fall into the transmission energy acceptance range 89. Note that the energy acceptance range is not to be confused with transmission detection windows 60 and 61, which are spatial windows. As a result, some of the emission activity impinging on the transmission detection windows 60 and 61 will be incorrectly detected as transmission activity, thereby introducing inaccuracy into the transmission image.

Consequently, the present invention includes a technique for reducing emission contamination in the transmission scan. Specifically, emission contamination detection windows 62 and 63 are defined on the imaging surfaces 12 and 13 of detectors 10 and 11, respectively, for detection of photons in an energy acceptance range centered at the photopeak of the transmission source (i.e., 662 keV if a $Cs^{137}$ transmission source is used). That is, both the transmission detection windows 60 and 61 and the emission contamination detection windows 62 and 63 have energy acceptance ranges centered at the transmission photopeak, as shown in FIG. 11B.

Figure 10:
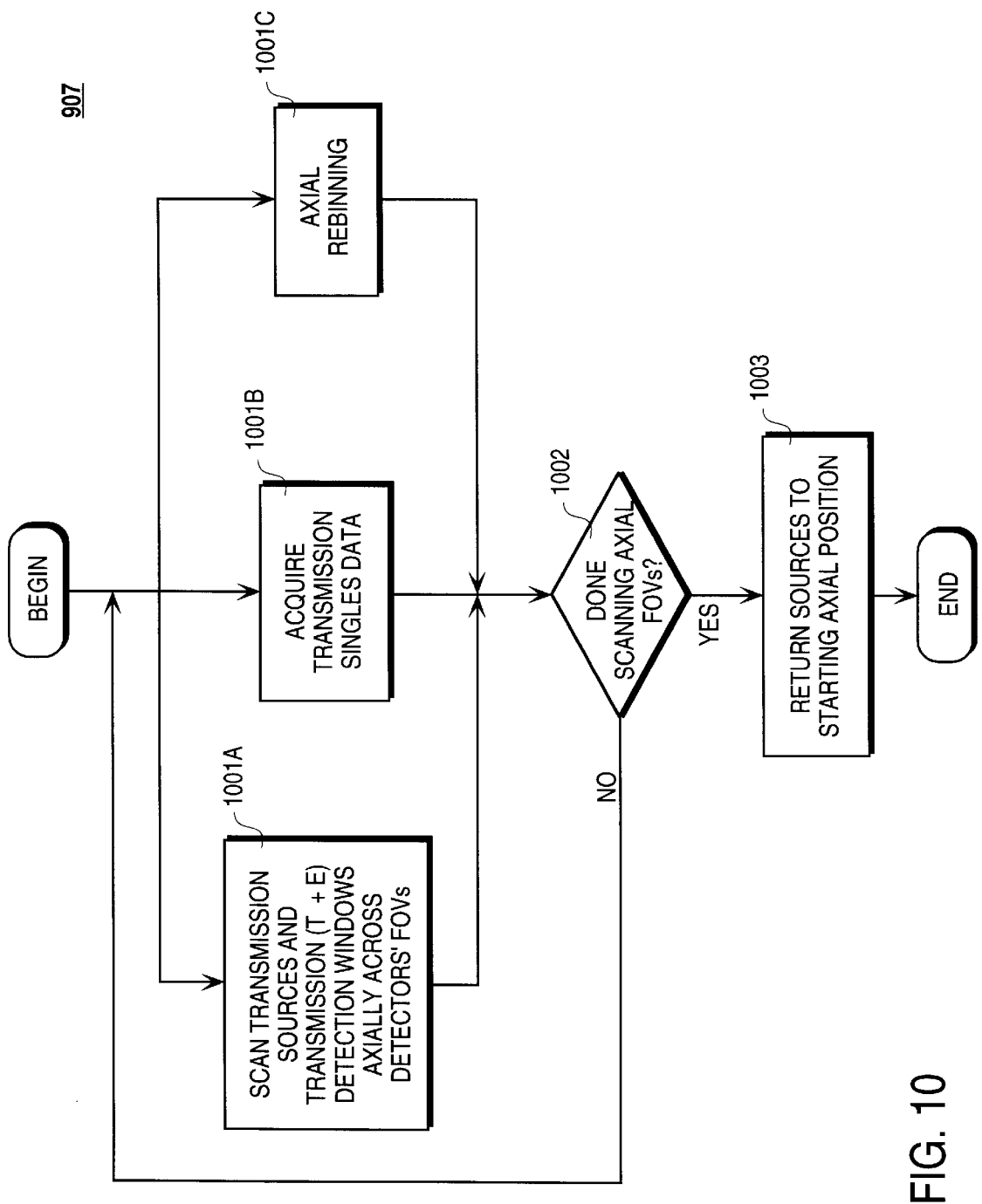
FIG. 10 is a flow diagram illustrating a routine for performing a transmission scan of an object.

Because the transmission detection windows 60 and 61 will receive some emission activity, those windows will henceforth be referred to in this description as the "T+E" (Transmission+Emission) windows 60 and 61 to facilitate description. Similarly, the emission contamination detection windows 62 and 63 (see FIGS. 5A, 5B, and 11) will henceforth be referred to as the "E" windows. Note that the emission singles rate falling within the transmission energy acceptance window does not change substantially over the short acquisition time period, regardless of whether the transmission beam is over the T+E window 60. Therefore, the emission count detected within the E window 62 can be used to subtract out the emission contamination within the T+E window 60. FIG. 10 illustrates in greater detail the step 907 (FIG. 9A) or 929 (FIG. 9B) of acquiring transmission data according to the above-mentioned technique.

At each angular stop, the transmission scan is characterized by three concurrent steps, 1001A, 1001B, and 1001C. In step 1001A, the transmission sources and the T+E detection windows 60 and 61 are scanned axially across the FOVs of the detectors 10 and 11, respectively. As the T+E windows 60 and 61 are scanned, transmission data is acquired in step 1001B based on radiation detected within the T+E windows 60 and 61 and rebinned into sinograms using an axial rebinning algorithm in step 1001C. This process repeats until the entire axial FOVs of detectors 10 and 11 have been scanned (step 1002), at which time the source assemblies 30 and 31 are returned to their initial axial positions in step 1003. Alternatively, after step 1002 the source assemblies 30 and 31 can be left at their final axial position and then scanned in the opposite direction axially for the next angular position of the detectors 10 and 11.

The present invention provides for a correction of emission contamination in the transmission scan by measuring the emission countrate at various positions and points in time and correcting for emission contamination on-the-fly (on an event-by-event basis) as the transmission scan is performed, as will be described in greater detail below. This technique includes defining the E windows 62 and 63 on the imaging surfaces 12 and 13 of detectors 10 and 11, respectively. The E windows 62 and 63 are scanned in synchronization with, but are offset axially from, the transmission T+E windows 60 and 61. For a given axial position of the E windows 62 and 63, the number of counts detected in the E windows 62 and 63 provides a good approximation of the emission activity impinging on the T+E windows 60 and 61 when the T+E windows 60 and 61 are located at the same position. Consequently, in accordance with one embodiment of the present invention, each time a count is detected in an E window of a detector, a count is removed from the corresponding location in a transmission projection buffer representing the data acquired in the T+E windows 60 and 61. The result is to effectively remove virtually all of the emission contamination from the transmission image.

Note that the fanbeam collimation of the point sources 30A and 31A enables this technique to be performed in conjunction with a singles transmission source. More specifically, the fanbeam collimation enables the simultaneous acquisition of both emission and singles transmission data with the same detector and on-the-fly correction. This technique is in contrast with prior techniques which make use of uncollimated coincidence sources and/or do not perform on-the-fly correction of emission contamination. See, e.g., R. J. Smith et al., "Simultaneous Post Injection Transmission and Emission Contamination Scans in a Volume Imaging PET scanner, " 1995 IEEE Nuclear Science Symposium and Medical Imaging Conference Record, Vol. 3, pages 1781–85, 1995, and R. J. Smith et al., "Post Injection Transmission Scanning in a Volume Imaging PET Camera," IEEE Transactions on Nuclear Science, vol. 41, No. 4, August 1994.

Figure 12A:
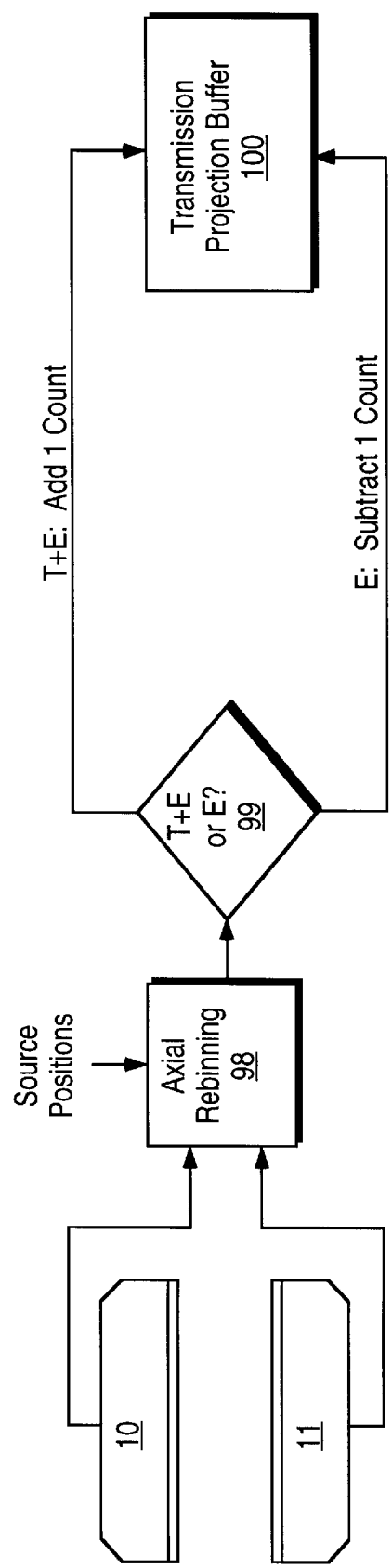
FIG. 12A is a block diagram illustrating a technique for correcting for emission contamination in a transmission image.

FIG. 12A further illustrates the above-described technique for correcting for emission contamination in the transmission scan. Transmission and emission radiation is detected by the detectors 10 and 11 using the scanning T+E and E detection windows, as described above. Information on the detected events (i.e., X and Y position and energy level Z) is provided to an axial rebinning algorithm 98, which receives as input the axial (z) positions of the sources 30A and 31A and the angular positions of the detectors and sources about the z axis. For each count detected in either the T+E window or the E window of one of the detectors 10 and 11, if the count was detected in an T+E window (block 99), then one count is added to the corresponding location in the transmission projection buffer 100, and if the count was detected within an E window, then one count is subtracted from the corresponding location in the transmission projection buffer 100. The counts subtracted from the transmission projection buffer 100 will substantially equate to the emission contamination counts undesirably added to the corresponding locations in the projection buffer 100. Note that the inputting of the source positions to axial rebinning algorithm 98 allows counts to be added or subtracted from the proper locations of the transmission projection buffer 100, such that correction of emission contamination can be performed on an event-by-event basis and in a spatially dependent manner.

Figure 12B:
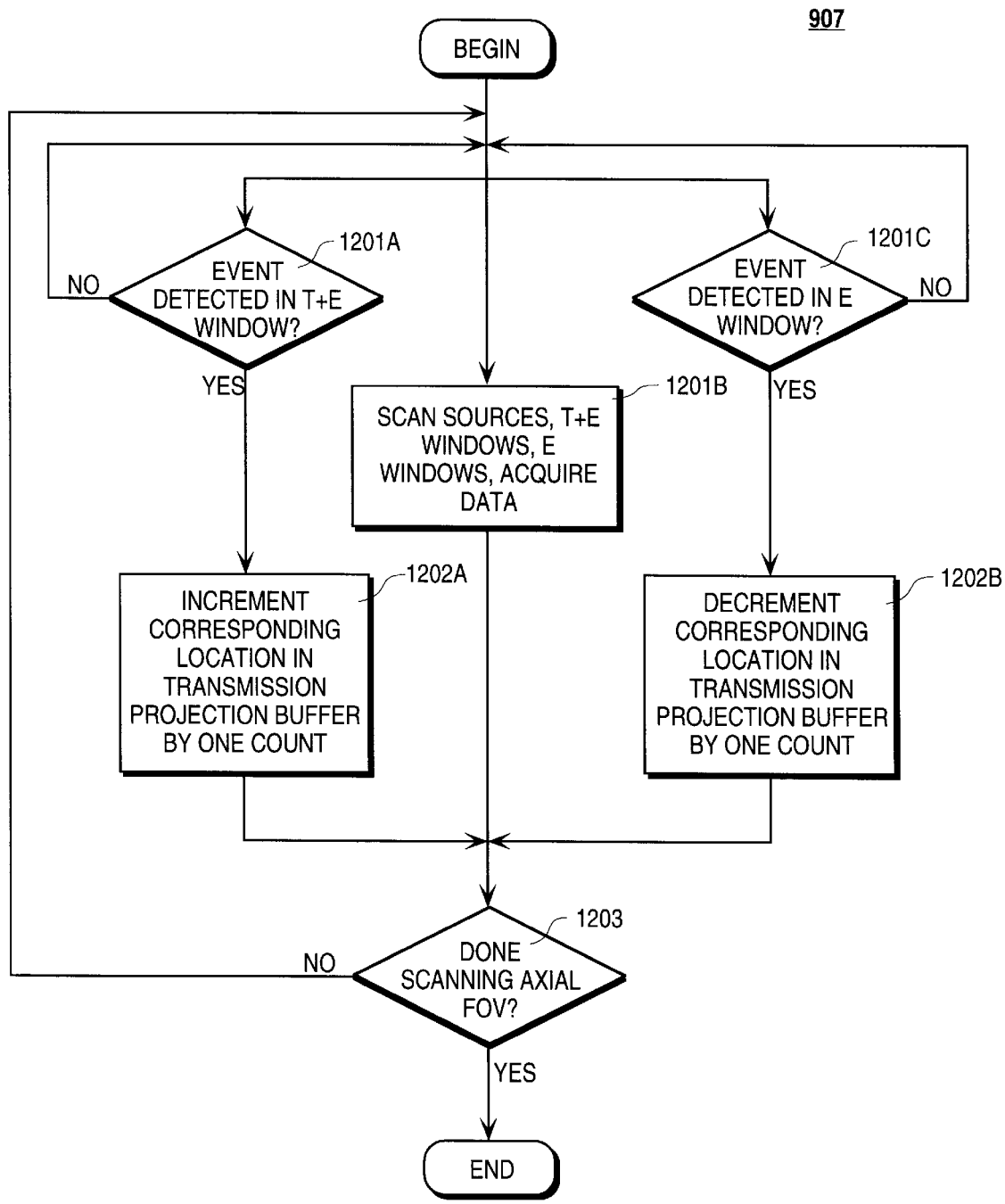
FIG. 12B is a flow diagram illustrating a routine for performing on-the-fly correction of emission contamination during a transmission scan.

FIG. 12B illustrates the step 907 (or 929) of performing the transmission scan according to an embodiment which uses emission contamination correction in accordance with FIG. 12A. The routine is characterized by three concurrent processing paths. In the first path, it is determined in step 1201A whether an event has been detected in a T+E window. If so, the corresponding location in the transmission projection buffer 100 is incremented by one count in step 1202A; if not, the processing path repeats from the beginning. In the second processing path, the transmission sources, T+E windows, and E windows are scanned axially across the FOVs of their respective detectors to acquire data in step 1201B. In the third processing path, it is determined in step 1201C whether an event has been detected in an E window. If so, the corresponding location in the transmission projection buffer 100 is decremented by one count in step 1202B; if not, the processing path repeats from the beginning. After performing either step 1202A, 1201B, or 1202B, then if the entire axial FOV has not been scanned, then the routine repeats from the beginning; otherwise, the routine ends.

Note that the width of the T+E and E windows can be varied based on axial position to achieve the best windowing effect, such as when a window reaches the edge of the imaging surface. However, for any given axial position, the width of the T+E and E windows remains constant to ensure accurate correction.

Deadtime Correction

Figure 13:
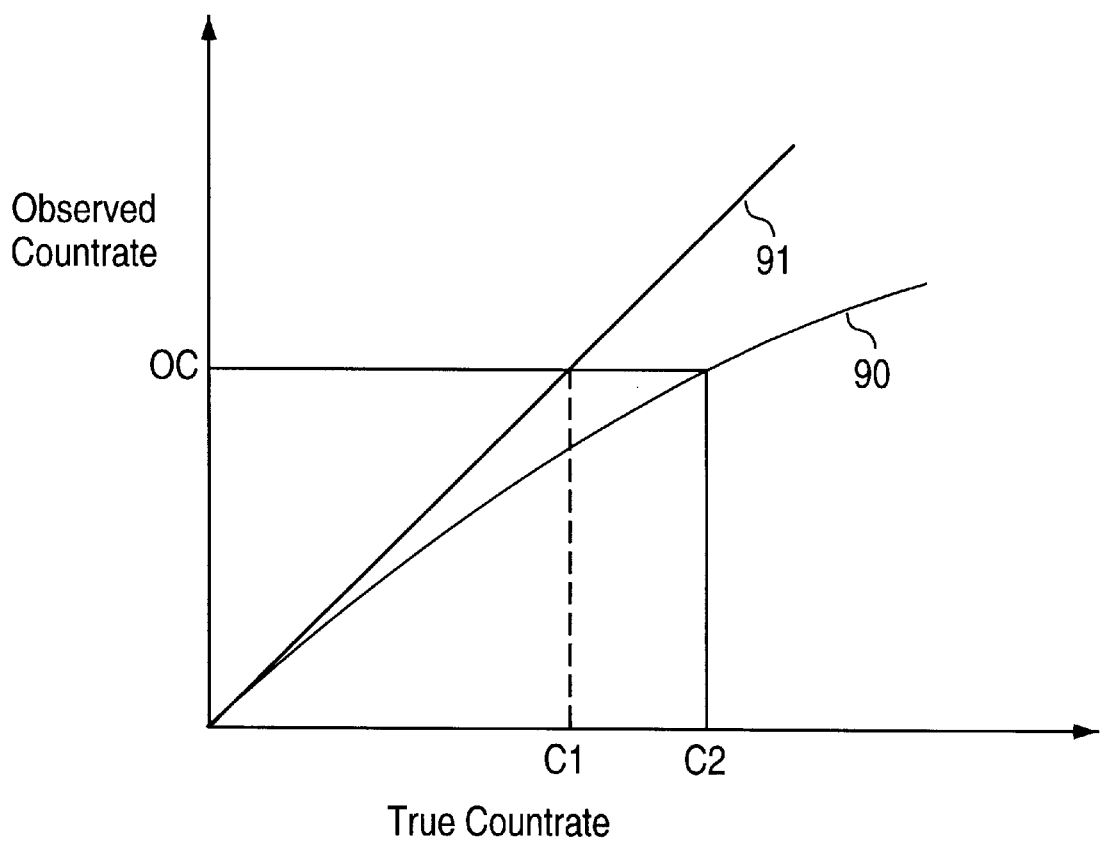
FIG. 13 is a graph illustrating effects of deadtime losses.

One problem associated with conventional gamma cameras is deadtime loss. Deadtime refers to the inability of a scintillation detector to distinguish two distinct scintillation events which occur very close together in time. Deadtime loss can be defined as the difference between the true countrate and the observed countrate which results from detector deadtime. FIG. 13 illustrates the effect of deadtime losses in the form of a plot of observed countrate against true countrate. Line 91 represents the ideal (but unrealistic) case in which there is no deadtime loss; in that case, the observed countrate OC equals the true countrate C1. In contrast, line 90 represents the response of a gamma camera system that is subject to deadtime loss; in that case, the observed countrate OC is lower than the true countrate C2. Note that the deadtime loss is dependent upon the singles rate; that is, as the singles rate (true countrate) increases the deadtime loss (difference between the true countrate and the observed countrate) also increases.

One known technique for correcting for deadtime loss is to apply a single, global correction factor, which is not applied until after the data has been acquired. See, e.g., R. J. Smith et al., "Simultaneous Post Injection Transmission and Emission Contamination Scans in a Volume Imaging PET scanner," 1995 IEEE Nuclear Science Symposium and Medical Imaging Conference Record, vol. 3, pages 1781–85, 1995. However, the use of a global correction factor does not account for the spatial dependency of deadtime losses. In particular, deadtime loss is dependent upon the singles rate, which is dependent upon both axial position and projection angle. Therefore, the use of a global deadtime correction factor may introduce inaccuracies into the transmission image.

Hence, the present invention includes a technique for correcting for deadtime losses which takes into account the spatial dependency of deadtime losses. More specifically, the present invention includes a technique for correcting for deadtime losses on an event-by-event basis (on-the-fly). Because deadtime is dependent upon the singles rate, a singles rate vs. deadtime calibration curve can be derived for a given gamma camera system. Hence, in accordance with the present invention, a deadtime versus singles rate calibration curve is empirically derived for the gamma camera system 1 and then used to create a look-up table of deadtime correction factors for various different singles rates. In one embodiment, each correction factor in the look-up table is a factor by which an observed count is multiplied during an imaging session before being added to the transmission projection, in order to compensate for deadtime losses. Higher singles rates will correspond to higher deadtime losses and, therefore, higher correction factors from the look-up table. The look-up table can be an integer map, which may be created to have a number of entries chosen so as not to compromise the speed of rebinning.

As an example of this technique, if the current singles rate corresponds to no significant deadtime loss, then the corresponding location in the transmission projection buffer can be increased by 50 counts, rather than one count, for each detected count. On the other hand, if there is a singles rate corresponding to a 2% deadtime loss, then the corresponding location in the transmission projection buffer can be increased by 51 counts rather than one count. Note that increasing the number of counts in this way introduces an artificial magnification factor in the transmission projection. The above example would introduce a magnification factor of 50 into the transmission projection. This magnification can be removed during reconstruction, however, by scaling down the image accordingly at that time. It should be noted that the accuracy of the deadtime correction depends upon the magnification factor selected, the accuracy of the initial calibration, and the assumption that there is little or no variance of deadtime within the transmission beam.

Figure 14A:
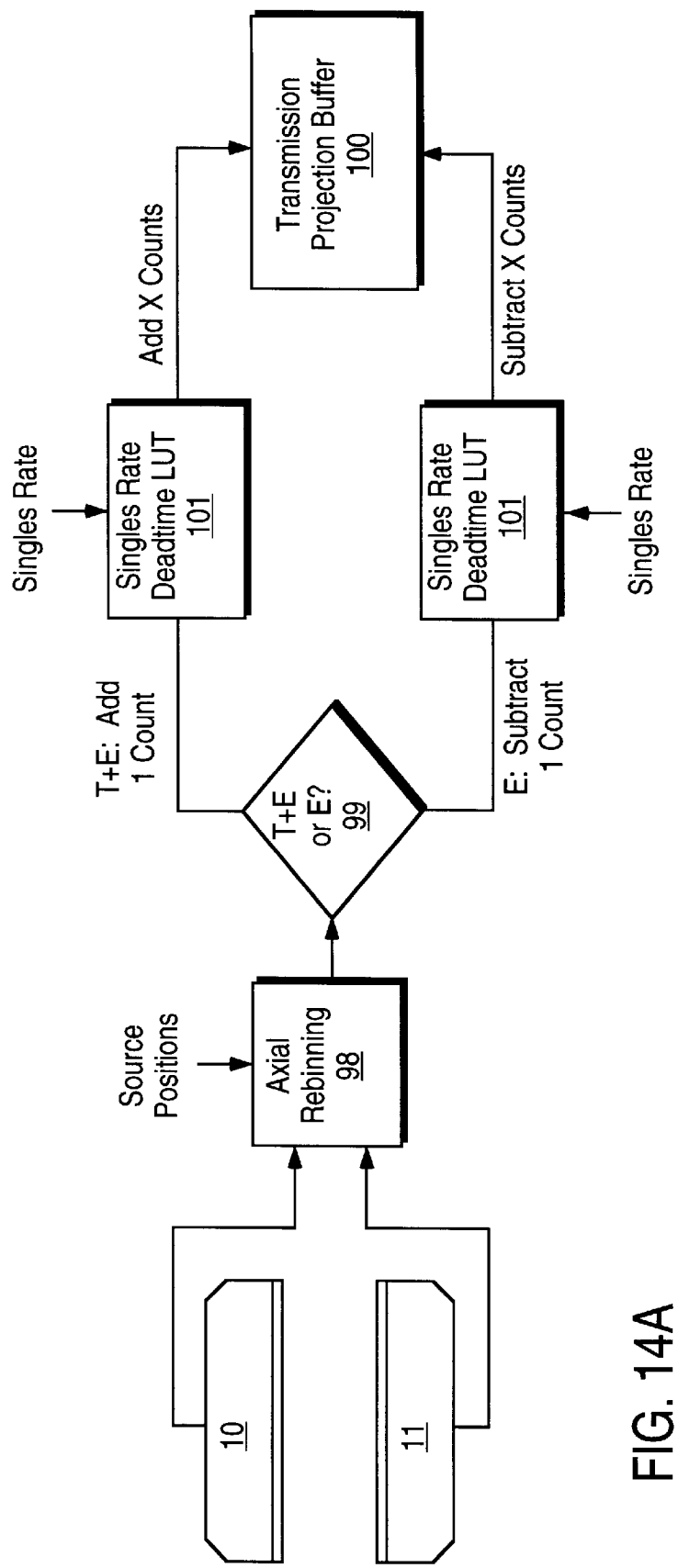
FIG. 14A is a block diagram illustrating a technique for performing on-the-fly correction of emission contamination and deadtime during a transmission scan.

FIG. 14A illustrates a technique for implementing deadtime correction on-the-fly, as described above. In one embodiment, this technique is implemented in conjunction with the emission contamination correction technique described above. Specifically, the process flow of FIG. 14A is essentially the same as that of FIG. 12A with the exception of the addition of the singles rate deadtime look-up tables (LUTs) 101. If a count is detected in a T+E window (block 99), then rather than adding one count to the appropriate location in the transmission projection buffer 100, as in the case of FIG. 12A, X counts are added to that location in the buffer, where X is determined from the singles rate deadtime look-up table 101 based on the current singles rate. Similarly, if an event is detected in the E window, then rather than subtracting a single count from the appropriate location in the transmission projection buffer, X counts are subtracted from that location, where X is determined from the singles rate deadtime look-up table 101 based on the current singles rate. Note that, in one embodiment, the singles rate used for this purpose is the global singles rate (i.e., the singles rate observed across an entire detector) rather than the singles rate within either a T+E window or an E window.

As with correction of emission contamination, the correction for deadtime loss is performed on an event by event basis. Accordingly, the source position (angular position about the z axis and axial position) is input to the axial rebinning algorithm 98 to enable each event to be associated with the appropriate location in the transmission projection buffer 100. This technique is in contrast with the above-mentioned technique in which a single, global correction factor is applied, which does not take into account the spatial dependency of deadtime losses.

Figure 14B:
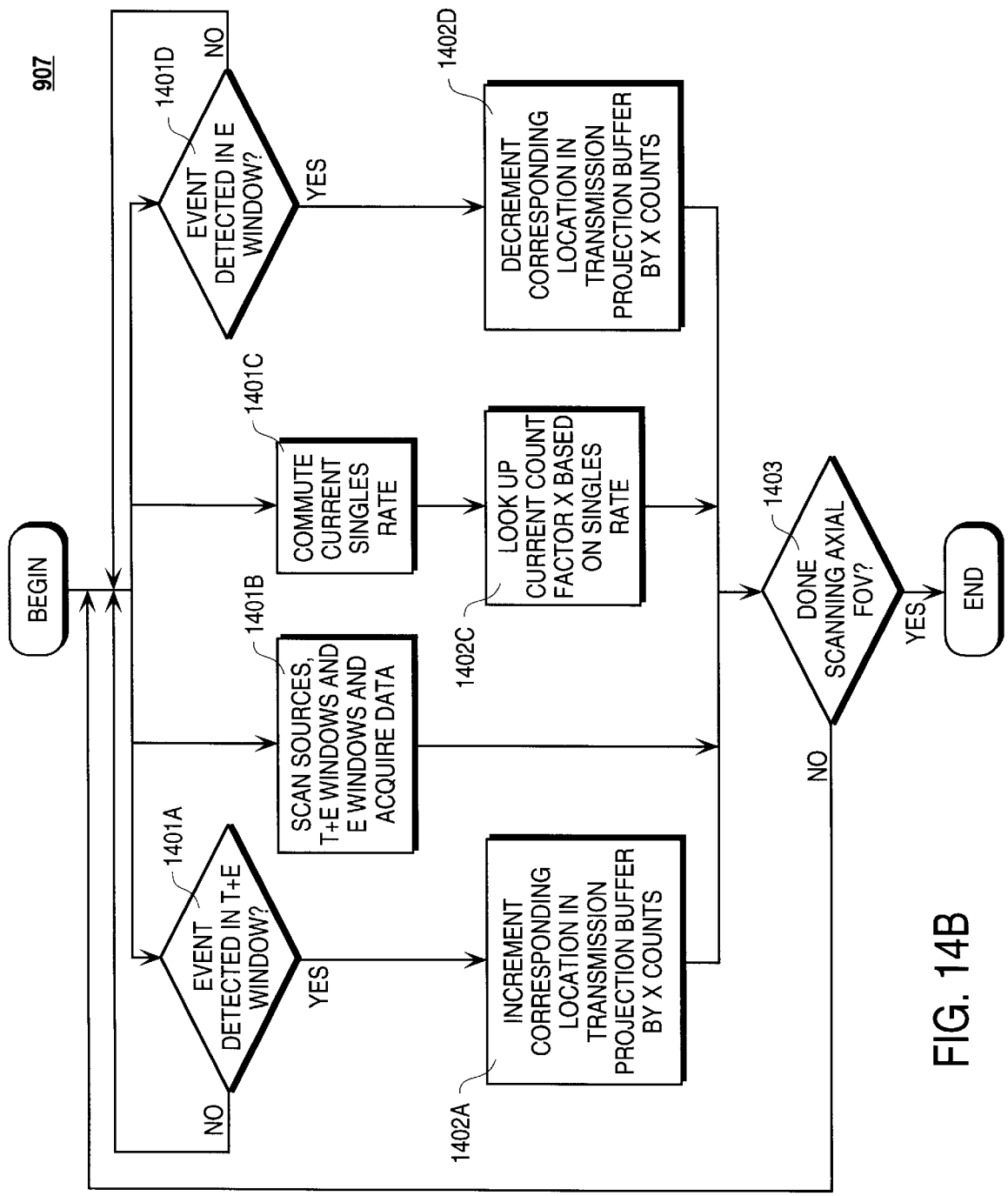
FIG. 14B is a flow diagram illustrating a routine for performing on-the-fly deadtime correction and emission contamination and deadtime during a transmission scan.

FIG. 14B illustrates the step 907 (or 929) of performing the transmission scan according to an embodiment which uses on-the-fly correction of both deadtime loss and emission contamination, as described above. The routine is characterized by four concurrent processing paths. In the first processing path, it is determined in step 1401A whether an event has been detected in a T+E window; if not, the processing path repeats from the beginning. If an event has been detected in the T+E window, then in step 1402A, the corresponding location in the transmission projection buffer 100 is incremented by X counts, where X is determined in another concurrent processing path, as will be described below. A second processing path consists of step 1401B, in which the transmission sources 30A and 31A, the T+E windows 60 and 61, and the E windows 62 and 63 are scanned axially to acquire data. A third processing path begins with step 1401D, in which it is determined whether an event has been detected in an E window; if not, the processing path repeats from the beginning. If an event has been detected in the E window, then in step 1402D the corresponding location in the transmission projection buffer 100 is decremented by X counts, where X is determined in the fourth concurrent processing path as follows. In the fourth concurrent processing path, the current singles rate is computed in step 1401C. As noted above, the singles rate in this embodiment is the global singles rate for the detectors 10 and 11 for this particular detector angle. Based on the current singles rate, the current count factor X is determined from the lookup table in step 1402C. After completion of any of the four concurrent processing paths, then the routine repeats from the beginning if the entire axial field of view has not yet been scanned (step 1403). Otherwise, the routine ends.

Figure 14C:
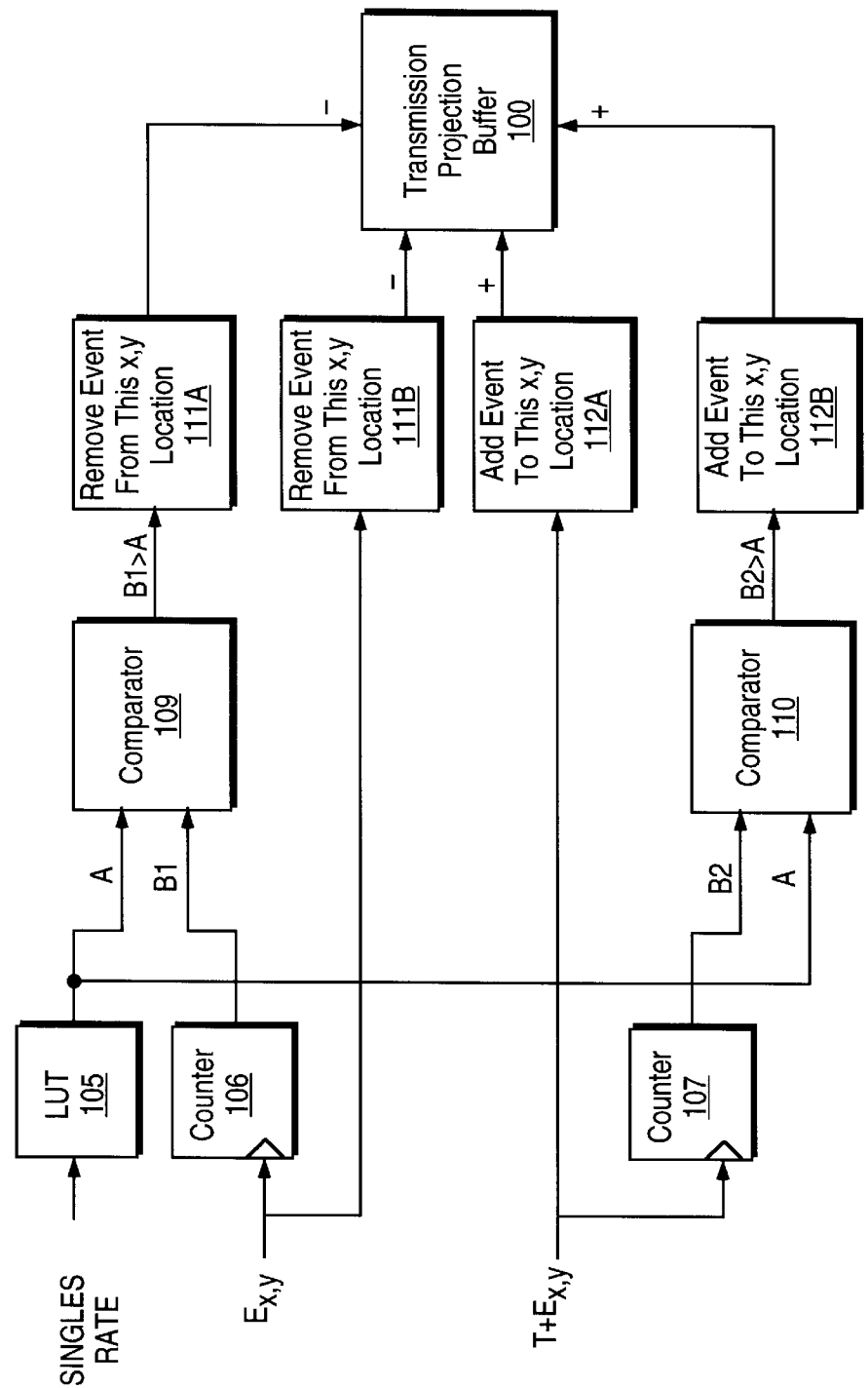
FIG. 14C is a block diagram illustrating an alternative technique for performing on-the-fly correction of emission contamination and deadtime during a transmission scan.

FIG. 14C shows an alternative embodiment for implementing on-the-fly deadtime correction and emission contamination correction. Note that the embodiment of FIG. 14C, as with other aspects of the present invention, can be implemented in software, hardware, or a combination thereof. As in the embodiments described above, both emission contamination correction and deadtime correction are performed on an event by event basis. In contrast with the embodiment of FIGS. 14A and 14B, however, each observed count is not multiplied by a factor in the embodiment of FIG. 14C. Rather, each count generally is represented as one count in the transmission projection buffer 100. However, additional counts may be added or subtracted to appropriate locations of the transmission projection buffer 100 depending upon the observed singles rate at a given point in time and the spatial window (T+E or E) in which a given count is detected.

The technique of FIG. 14C includes a look-up table 105, which outputs a value A that is based on the current singles rate. The technique also includes counters 106 and 107, each of which counts up in response to its clock input to a maximum value MAXCOUNT and then automatically resets to zero. Counter 106 is clocked by signal $E_{x,y}$, which is asserted each time an event is detected in the E window. Counter 106 outputs a signal B1. Similarly, counter 107 receives a signal $T+E_{x,y}$ at its clock input, which is asserted each time an event is detected in the T+E window, and outputs a signal B2.

The technique of FIG. 14C also includes two comparators 109 and 110. Comparator 109 receives as input signals A and B1 and asserts its output signal when B1 is greater than A (i.e., when the output of counter 106 exceeds the output of look-up table 105). Comparator 110 receives as input signals A and B2, and asserts its output when B2 is greater than A (i.e., when the output of counter 107 exceeds the output of look-up table 105).

Look-up table 105 is generated in a manner similar to that described above in connection with FIGS. 14A and 14B. That is, look-up table 105 is created based on empirical data and provides output signal A having a value based on the global input singles countrate. Specifically, the value A output by look-up table 105 is based on the following equation:

$$A = MAXCOUNT*(COUNTRATE_{observed} + (COUNTRATE_{true} - COUNTRATE_{observed})/2)$$

where:
$COUNTRATE_{true}$ is the true countrate if the deadtime were zero,
$COUNTRATE_{observed}$ is the intrinsic observed countrate, and
MAXCOUNT is the maximum value of the free running counters 106 and 107.

Each time an event is detected in the T+E window (i.e., each time $T+E_{x,y}$ is asserted), block 112A causes one event to be added to the appropriate x,y location of transmission projection buffer 100. In addition, if B2 is greater than A, block 112B causes an additional event to be added to the appropriate x,y location of transmission projection buffer 100 in response to assertion of signal T+$E_{x,y}$. Adding such additional events compensates for deadtime losses. However, events must also be removed from transmission projection buffer 100 to correct for emission events detected in the T+E window. Accordingly, each time an event is detected in the E window (i.e., each time $E_{x,y}$ is asserted), block 111B causes one event to be subtracted from the corresponding location in the transmission projection buffer 100. In addition, if B1 is greater than A, block 111A causes an additional event to be subtracted from the corresponding x,y location in the transmission projection buffer 100 in response to assertion of signal $E_{x,y}$. Hence, the technique illustrated in FIG. 14C provides correction on an event-by-event basis of both deadtime losses and emission contamination in the transmission scan.

Note that the predetermined contents of the look-up table 105 as well as the value of MAXCOUNT will determine the actual response of the illustrated embodiment (i.e., how frequently additional events will be added or subtracted to/from the transmission projection for a given singles rate). As in the embodiments discussed above, this technique is advantageous in comparison to previous techniques which do correct for the spatial variances in deadtime or emission contamination.

Transmission Self-Contamination

Another factor which can cause degradation of image quality is self-contamination of the transmission scan. Transmission self-contamination refers to the detection of transmission radiation by a detector which is not the intended target of the source from which the radiation originates. More specifically, referring to FIG. 7, transmission self-contamination includes radiation transmitted by source 30A that is unintentionally detected by detector 10 and radiation transmitted by source 31A that is unintentionally detected by detector 11. The present invention provides certain features to reduce such contamination.

Mounting the sources 30A and 31A outside the FOVs of the detectors 10 and 11 serves to reduce the likelihood of transmission self-contamination, as does proper shielding within source assemblies 30 and 31, in which sources 30A and 31A are enclosed. A third technique for reducing transmission self-contamination is to quantify that self-contamination and subtract it out from the transmission image. This form of calibration can be performed by performing a transmission scan in which only the source that is closest to the detector to be calibrated is transmitting. That source as well as the T+E and E windows on the detector to be calibrated are then scanned across the FOVs of the detectors. Two images are generated for each detector based on this calibration scan, one image for the transmission self-contamination in the T+E window, and one for the transmission self-contamination in the E window. Note that if the translation of the transmission source is nonuniform inside the FOV, it may also be necessary to correct for the differences in count densities that result from this effect. After the two images are acquired, they are low-pass filtered and stored in a buffer, such that they are accessible to the rebinning algorithm.

Correction of the transmission self-contamination can be performed by subtracting the difference between the self-contamination calibration projections (i.e., T+E projection minus E projection) from the transmission projections and then reconstructing the transmission projections.

Randoms Correction

Another problem encountered in PET imaging system is that of random coincidences ("randoms"). PET imaging systems produce images based upon the detection of coincidence events. Coincidence events are normally identified as two events observed by opposing detectors which occur within a relatively narrow time window. However, some pairs of events detected within this time window are not the result of true coincidences (i.e., based on a single positron-electron annihilation) but are based on separate annihilation or Compton events. The misinterpretation of such randoms as true coincidences contributes to inaccuracies in the imaging process and, therefore, degrades image quality.

One known technique for providing randoms correction is a direct measurement technique in which a parallel time circuit for the coincidence detection circuit is provided with a time delay on the signal from one detector. The delay is made large enough so that no true coincidence events are registered in the parallel time circuit. As a result, events which are detected in the parallel time circuit can result only from random coincidences, which can then be subtracted from those counted as true coincidences. One problem with this technique, however, is that it tends to be a relatively complex hardware solution that adds to the cost and size of the gamma camera system. In addition, since this solution is based on direct measurement of (random) coincidences, and coincidences represent only a small fraction of the overall countrate, the resulting randoms data that is acquired tends to be noisy. Another approach is to form an estimate of the randoms based upon a mathematical model; however, because that approach is based upon an estimate, it is inherently subject to inaccuracies. For example, such an estimate might not take into consideration the spatial variations of randoms. Hence, the present invention provides a technique for correcting for randoms which overcomes these disadvantages.

In general, randoms R can be calculated according to the equation R=S1*S2*W, where S1 represents the singles rate from one detector, S2 represents the singles rate from the other detector, and W (also known as 2τ) represents the duration of the coincidence time window. In accordance with the present invention, each of the detectors 10 and 11 is treated as a collection of multiple subdetectors, each having a singles rate that is a subset of the overall singles rate (S1 or S2). For example, referring to FIG. 15, the total singles rate S1 for detector 10 can be expressed as:

$$S1 = S11 + S12 + S13 + \ldots + S1n.$$

Similarly, the total singles rate S2 for detector 11 can be expressed as:

$$S2 = S21 + S22 + S23 + \ldots + S2n.$$

Therefore, the total randoms R can be expressed as:

$$\begin{aligned} R &= (S11 + S12 + \ldots + S1n) * (S21 + S22 + \ldots + S2n) * W \\ &= (S11 * S21 + S11 * S22 + \ldots + S1n * S2n) * W \\ &= R1 + R2 + \ldots + R(n*n) \end{aligned}$$

where Ri (i=1, 2, . . ., (n*n)) is the randoms caused by any subcombination of a subdetector from detector 10 and a subdetector from detector 11. Thus, the above equation represents the concept that the global randoms are simply the sum of all the randoms contributed by each subdetector element pair.

Figure 16:
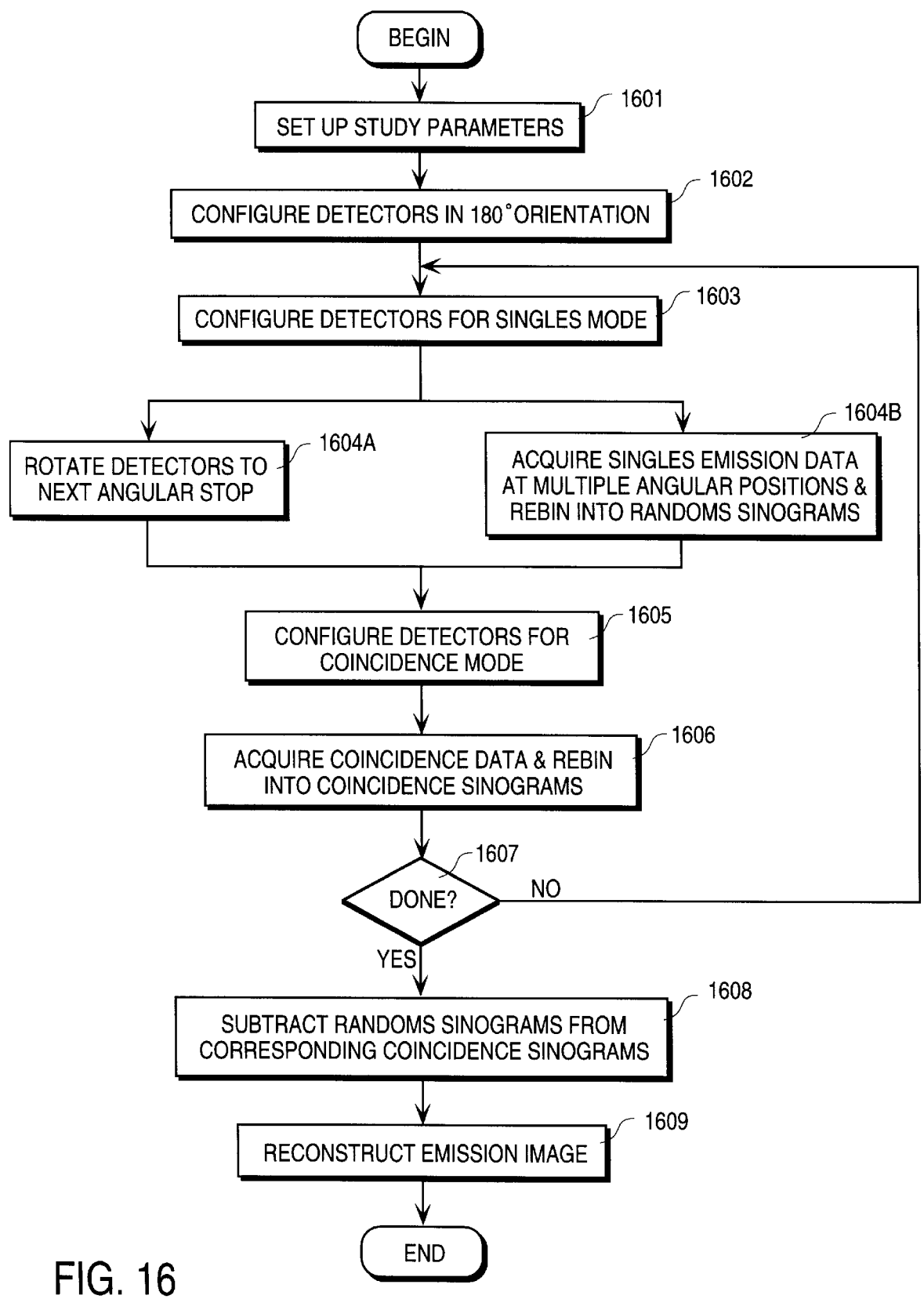
FIG. 16 is a flow diagram illustrating a routine for correcting for randoms during coincidence imaging.

In accordance with the present invention, by applying the concept of the above equation, a randoms sinogram can be obtained, which can be used to subtract out the randoms from the emission data. FIG. 16 illustrates a routine for performing randoms correction using this technique. In step 1601, the study parameters (i.e., number of angular stops and acquisition time at each stop) are set up as described above. In step 1602, detectors 10 and 11 are configured in a 180° degree orientation about the z axis, and in step 1603 the detectors are configured for acquisition in singles-mode. Next, the detectors are rotated to the first (or next) angular stop in step 1604A. Concurrently with rotating the detectors to the next angular stop, emission data is acquired in singles-mode and rebinned into randoms sinograms in step 1604B. In one embodiment, the data is acquired in step 1604B in the form of a number of "snapshots" taken at various angular positions between two angular stops. After the detectors have been rotated to the next angular stop and the singles data have been acquired, the detectors are configured for acquisition in coincidence mode in step 1605. Next, coincidence data is acquired and rebinned into coincidence sinograms in step 1606 for the prescribed time interval. If emission data have been acquired at all of the angular stops (step 1607), then the routine proceeds to step 1608, in which the randoms sinograms are subtracted from the corresponding coincidence sinograms. If there are additional angular stops, then the routine repeats from step 1603, in which the detectors are temporarily reconfigured for singles mode. After subtracting out the randoms, the emission image is reconstructed in step 1609.

Figure 15:
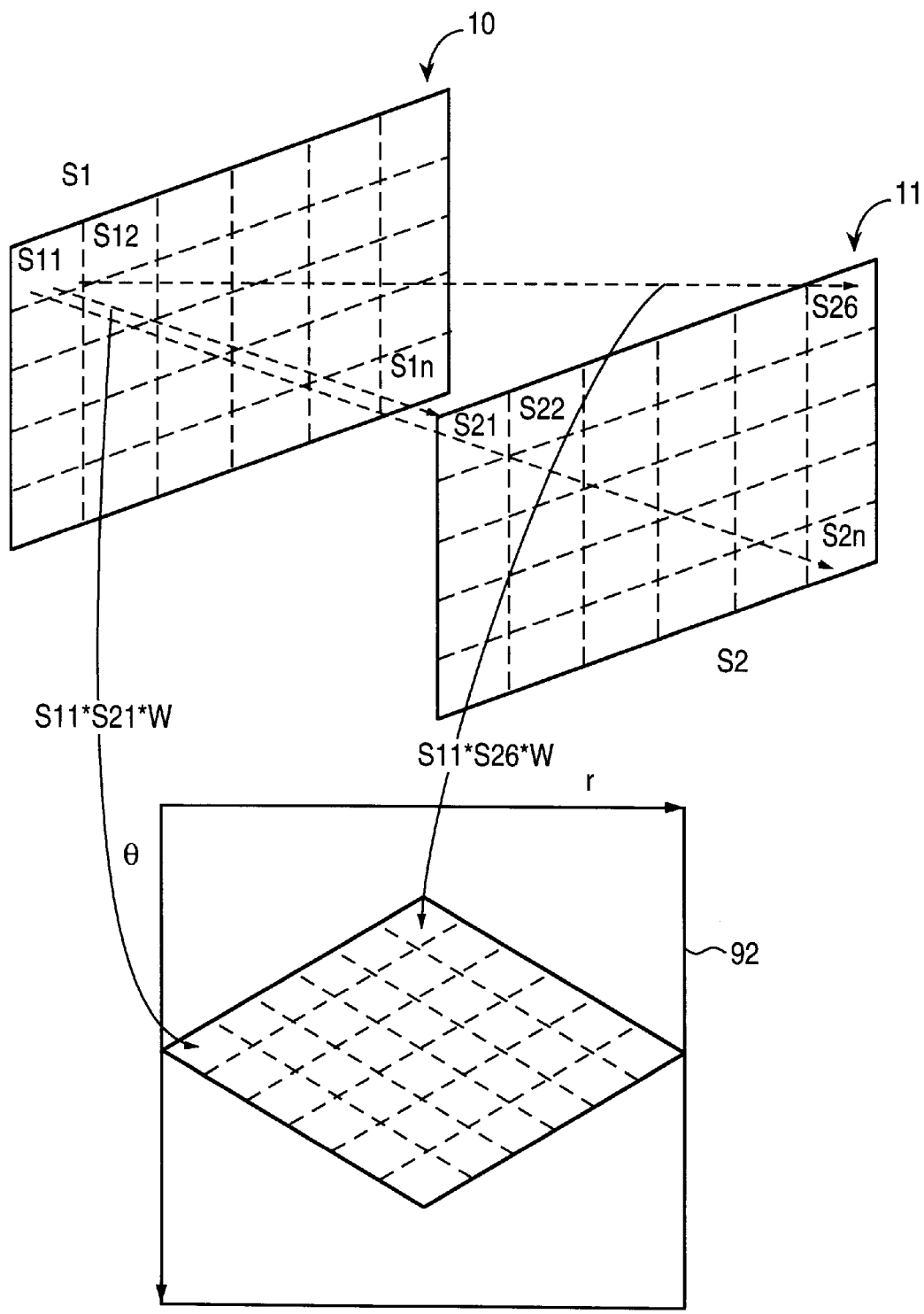
FIG. 15 illustrates a technique for rebinning singles events into a randoms sinogram.

FIG. 15 illustrates how the singles rate data is rebinned into a randoms sinogram. Detector 10 is divided into n virtual subdetectors S11, S12, ... S1n and detector 11 is divided into n virtual subdetectors S21, S22, ... S2n. Counts detected by detectors 10 and 11 are rebinned into randoms sinogram 92. For each detector angle about the z axis, the rebinned data appears as a diamond in the randoms sinogram. The final random sinogram is a summation of all the individual sinograms for each axial position. In one embodiment, the single-slice rebinning technique is used in the axial direction.

Note that the singles rate is much higher than the coincidence rate. Accordingly, a comparatively small period of time is required to acquire the singles data for purposes of randoms correction than is required to acquire the total emissions data. For example, for a coincidence fraction equal to 5% of the singles rate, the acquisition of singles would require only 1/20 of the total emission acquisition time. Thus, for a 20 minute total emission scan time, for example, only one minute of total detector rotation time would be required to acquire singles data for randoms correction.

It will be recognized that the randoms correction technique of the present invention takes into consideration and corrects for spatial variations in randoms by detecting the spatial variations in the singles. However, it should also be noted that, because randoms generally do not yield high frequency data in comparison to true coincidences, the randoms data can be stored in a matrix that is smaller than the normal emission projection matrix. For example, a 32×32×48 matrix may be used for randoms data as compared to a 128×128×96 matrix for the normal emission projection. The randoms matrix can then be expanded during correction.

It should also be noted that, in practice, calculating randoms R as S1*S2*W may not hold true. Therefore, it may be desirable to modify this equation using a calibration factor, i.e., R=Cal(S1, S2)*S1*S2*W, where Cal(S1,S2) is a calibration factor that may or may not depend upon S1 and S2. This calibration factor can be modeled as an empirical function that is derived using measurements with simple phantoms.

Thus, a dual-mode gamma camera system which utilizes single-photon transmission scanning to provide attenuation correction of PET data has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A nuclear camera system comprising:

a pair of detectors for detecting scintillation events;

a pair of single-photon radiation point sources for transmitting radiation through an object, each to a corresponding one of the detectors;

means for supporting the detectors to allow detection of radiation from a plurality of angular positions about an axis of rotation;

means for supporting the radiation point sources to allow transmission of radiation from a plurality of angular positions about the axis of rotation, such that each of the radiation point sources is fixed relative to the corresponding detector about the axis of rotation; and means for switchably controlling the detectors for acquisition of emission data in either single-photon mode or coincidence mode;

means for controlling the radiation sources to perform a transmission scan to acquire transmission data of the object, the transmission scan having a field of view associated therewith, the field of view defining a first region, a gap in the field of view defining a second region disposed within the first region;

means for correcting the coincidence emission data for attenuation using the transmission data; and means for controlling a table supporting the object, including means for causing the table to be moved during the transmission scan relative to the axis of rotation based on positions of the pair of detectors about said axis of rotation to allow acquisition of transmission data of portions of the object which would otherwise be located within the gap in the field of view.

2. A nuclear camera system according to claim 1, wherein the pair of detectors includes a first detector and a second detector, wherein the pair of radiation point sources includes a first point source and a second point source, the nuclear camera system further comprising:

means for defining a first transmission detection window within a portion of a field of view of the second detector;

means for defining a second transmission detection window within a portion of the field of view of the first detector;

means for scanning radiation from the first point source across the field of view of the second detector in a fanbeam profile in synchronization with the first transmission detection window in a direction substantially parallel to the axis of rotation; and means for scanning radiation from the second point source across the field of view of the first detector in a fanbeam profile in synchronization with the second transmission detection window in a direction substantially parallel to the axis of rotation.

3. A nuclear camera system according to claim 1, wherein during the transmission scan:

the point sources remain fixed along the axis of rotation relative to the detectors while the point sources are transmitting; and each of the point sources illuminates a corresponding one of the detectors, such that an illuminated portion of the corresponding detector has a fixed position along the axis of rotation while the corresponding source is transmitting.

4. A nuclear camera system according to claim 1, wherein the first region and the second region are areas within a plane that is perpendicular to the axis of rotation.

5. A nuclear medicine imaging system comprising:

a first detector and a second detector for detecting scintillation events, the first and second detectors each having an imaging surface;

a first radiation point source and a second radiation point source for transmitting radiation;

a gantry supporting the first and second detectors and the first and second radiation point sources, such that the first and second detectors and the first and second radiation point sources are rotatable about an axis of rotation; and a processing system coupled to selectably control the detectors and the radiation point sources for acquisition of emission image data in either a single-photon mode or a coincidence mode, the processing system controlling the detectors to acquire coincidence emission data of the object, the processing system further controlling the radiation point sources to acquire transmission data of the object during a transmission scan, including defining a first transmission detection window within a portion of the field of view of the second detector and defining a second transmission detection window within a portion of the field of view of the first detector, and scanning radiation from the first radiation point source across the field of view of the second detector in a fanbeam profile in synchronization with the first transmission detection window and scanning radiation from the second radiation point source across the field of view of the first detector in a fanbeam profile in synchronization with the second transmission detection window, wherein the processing system corrects the coincidence emission data for attenuation using the transmission data, wherein the processing system is coupled to control a table supporting the object, the processing system causing the table to be displaced during the transmission scan relative to the axis of rotation based on positions of the first and second detectors about said axis of rotation to allow acquisition of transmission data of the object corresponding to a gap in a field of view of the transmission scan, the transmission field of view defining a first area in a plane perpendicular to the axis of rotation, the gap defining a second area in the plane, the second area disposed within the first area.

6. A nuclear medicine imaging system according to claim 5, wherein radiation from the first and second radiation point sources is scanned using a translation of the first and second radiation point sources.

7. A nuclear medicine imaging system according to claim 5, wherein the first and second radiation point sources each have a radiation shield including a revolving aperture, and wherein radiation from the first and second radiation point sources is scanned using movement of the revolving apertures.

8. A nuclear medicine imaging system according to claim 5, wherein the angular position of the first radiation point source about the axis of rotation is fixed relative to the angular position of the second detector about the axis of rotation, and the angular position of the second radiation point source about the axis of rotation is fixed relative to the angular position of the first detector about the axis of rotation.

9. A nuclear medicine imaging system according to claim 5, wherein the first radiation point source and the second radiation point source are positioned on the same side of an axis that is perpendicular to both the axis of rotation and to the imaging surfaces of both the first and second detectors.

10. In a nuclear camera system including a plurality of scintillation detectors, a plurality of single-photon point sources, and circuitry configurable to detect and record scintillation events in either a coincidence mode or a single-photon mode, a method of generating an image of an object, the method comprising the steps of:

performing an emission scan of the object by acquiring coincidence emission data of the object from a plurality of angular positions about an axis, including rotating the detectors through the plurality of angular positions about the axis;

performing a transmission scan of the object by acquiring transmission data at each of the plurality of angular positions using at least one of the detectors and at least one of the single-photon point sources, including maintaining a fixed position of each of the single-photon point sources about the axis relative to the plurality of detectors;

repeatedly adjusting a position of the object relative to the axis during the transmission scan according to the angular positions of the single-photon point sources and the detectors about the axis to allow acquisition of transmission data of portions of the object which would otherwise be located within a gap in a field of view of the transmission scan, the field of view defining a first area in a plane perpendicular to the axis, the gap defining a second area in the plane, the second area disposed within the first area;

correcting the coincidence emission data for attenuation using the transmission data; and reconstructing an emission image using the attenuation corrected coincidence emission data.

11. A method according to claim 10, further comprising the step of maintaining the point sources in a fixed position relative to the detectors while acquiring transmission data at each of the angular positions.

12. A method according to claim 10, wherein the plurality of detectors includes a first detector and a second detector, wherein the plurality of point sources includes a first point source and a second point source, the step of acquiring transmission data comprising the steps of:

defining a first transmission detection window within a portion of the field of view of the second detector and defining a second transmission detection window within a portion of the field of view of the first detector;

scanning radiation from the first radiation point source across the field of view of the second detector in a direction substantially parallel to the axis in synchronization with the first transmission detection window using a fanbeam illumination profile; and means for scanning radiation from the second radiation point source across the field of view of the first detector in a direction substantially parallel to the axis in synchronization with the second transmission detection window using a fanbeam illumination profile.

13. An imaging system for generating images of an object, the imaging system comprising:
   a first source for transmitting radiation;
   a first detector for detecting radiation;
   a gantry for movably supporting the first detector and the first source and for positioning the first detector and the first source in a first plurality of positions about an axis of rotation, the first plurality of positions at least partially determining a transmission field of view associated with a transmission scan of the object, the transmission field of view defining a first region, a gap in the field of view defining a second region disposed within the first region;
   means for operating the first source and the first detector to acquire transmission data of the object during a transmission scan; and
   means for moving the object during the transmission scan based on the first plurality of positions about the axis of rotation to allow acquisition of transmission data of portions of the object corresponding to the gap in the transmission field of view.

14. An imaging system according to claim 13, further comprising:
   a second source for transmitting radiation;
   a second detector for detecting radiation; and
   means for operating the second source and the second detector to acquire transmission data of the object during the transmission scan;
   wherein the gantry is further for movably supporting the second detector and the second source and for positioning the second detector and the second source in a second plurality of positions about the axis of rotation, the second plurality of positions at least partially defining the transmission field of view.

15. An imaging system according to claim 14, wherein the first and second detectors each have an imaging surface, and wherein the first and second sources are positioned on the same side of an axis that is perpendicular to both the axis of rotation and to the imaging surfaces of both the first and second detectors.

16. An imaging system according to claim 14, further comprising means for operating the first and second detectors to acquire emission data corresponding to radiation emitted from the object, the transmission data for use in correcting the emission data.

17. An imaging system according to claim 16, wherein the means for operating the first and second detectors to acquire emission data comprises means for operating the first and second detectors to acquire coincidence emission data, the transmission data for use in correcting the coincidence emission data.

18. An imaging system according to claim 17, wherein each of the first and second sources comprises a single-photon point source.

19. An imaging system according to claim 17, wherein the means for operating the first source and the first detector to acquire transmission data comprises:
   means for defining a transmission detection window on an imaging surface of the first detector; and
   means for scanning radiation from the first source across the imaging surface of the first detector substantially parallel to the axis of rotation in a fanbeam profile in synchronization with the transmission detection window to acquire the transmission data.

20. An imaging system according to claim 13, wherein the first region and the second region are areas within a plane that is perpendicular to the axis of rotation.

21. A nuclear medicine imaging system comprising:
   a plurality of detectors for detecting radiation emitted from an object;
   a plurality of radiation sources for transmitting radiation through the object, each source for transmitting radiation to a corresponding one of the detectors;
   a gantry rotatably supporting the detectors and the radiation sources about an axis of rotation and configured to position the detectors and the radiation sources in a plurality of positions about the axis of rotation, wherein the plurality of positions of the detectors and the sources collectively determine a transmission field of view of the imaging system, the transmission field of view defining a first area, a gap in the field of view defining a second area disposed within the first area; and
   a processing system coupled to the detectors and the radiation sources, wherein the processing system is configured to control the detectors to acquire coincidence emission data of the object, wherein the processing system is further configured to control the radiation sources to acquire transmission data of the object during a transmission scan, wherein the processing system is further configured to correct the coincidence emission data using the transmission data, and wherein the processing system is further configured to cause a support element supporting the object to be displaced from the axis of rotation during the transmission scan based on the plurality of positions of the sources and the detectors, to allow acquisition of transmission data of portions of the object which would otherwise be located in the gap in the transmission field of view.

22. A nuclear medicine imaging system according to claim 21, wherein each of the radiation sources comprises a single-photon point source.

23. An imaging system according to claim 22, wherein each of the detectors has an imaging surface, and wherein the single-photon point sources are positioned on the same side of an axis that is perpendicular to both the axis of rotation and to the imaging surface of each of the detectors.

24. A nuclear medicine imaging system according to claim 23, wherein the processing system is further configured to define a transmission detection window within a portion of an imaging surface of one of the detectors, and wherein radiation from one of the radiation sources is scanned across a field of view of said one of the detectors in a direction substantially parallel to the axis of rotation in a fanbeam illumination profile in synchronization with the first transmission detection window to acquire the transmission data.

25. A nuclear medicine imaging system according to claim 23, wherein radiation from said one of the radiation sources is scanned along the field of view of said one of the detectors by a translation of the radiation source along the field of view of said one of the detectors.

26. A nuclear medicine imaging system according to claim 23, wherein the radiation source has a radiation shield including an aperture, and wherein radiation from said one of the radiation sources is scanned along the field of view of said one of the detectors by rotating the aperture.

27. A nuclear medicine imaging system according to claim 21, wherein the first area and the second area are defined within a plane that is perpendicular to the axis of rotation.

28. In a medical imaging system, a method of performing a transmission scan to acquire transmission data of an object, the medical imaging system including a plurality of radiation sources and a plurality of radiation detectors, the method comprising:

positioning the radiation sources and the radiation detectors in a plurality of positions about an axis;

operating the radiation sources and the radiation detectors at each of the plurality of positions to acquire the transmission data, the plurality of positions at least partially determining a transmission field of view associated with the transmission scan, the transmission field of view defining a first region, a gap in the field of view defining a second region disposed within the first region; and moving the object based on said positioning to allow acquisition of transmission data of portions of the object corresponding to the gap in the transmission field of view for each of the plurality of positions about the axis.

29. A method according to claim 28, wherein said operating the radiation sources and the radiation detectors comprises, for each of the plurality of positions:

defining a transmission detection window within a portion of an imaging surface of each of the radiation detectors;

scanning radiation from each of the radiation sources across the imaging surface of a corresponding one of the detectors in a fanbeam profile in synchronization with the corresponding transmission detection window.

30. A method according to claim 29, further comprising:

operating the radiation detectors to acquire emission data representing radiation emitted from the object;

using the transmission data to correct the emission data.

31. A method according to claim 28, wherein the first region and the second region are areas within a plane that is perpendicular to the axis.

* * * * *